(12) United States Patent
Ono et al.

(10) Patent No.: US 10,478,077 B2
(45) Date of Patent: Nov. 19, 2019

(54) BLOOD PRESSURE METER

(71) Applicant: OMRON HEALTHCARE Co., Ltd., Kyoto (JP)

(72) Inventors: Kenji Ono, Kyoto (JP); Yuma Adachi, Kyoto (JP); Yoshihide Tokko, Kyoto (JP); Eisuke Yamazaki, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 0 days.

(21) Appl. No.: 15/876,002

(22) Filed: Jan. 19, 2018

(65) Prior Publication Data

US 2018/0140209 A1   May 24, 2018

Related U.S. Application Data

(63) Continuation of application No. PCT/JP2017/019568, filed on May 25, 2017.

(30) Foreign Application Priority Data

Jul. 5, 2016   (JP) ................... 2016-133563

(51) Int. Cl.
*A61B 5/02* (2006.01)
*A61B 5/022* (2006.01)
(Continued)

(52) U.S. Cl.
CPC .......... *A61B 5/02233* (2013.01); *A61B 5/022* (2013.01); *A61B 5/023* (2013.01);
(Continued)

(58) Field of Classification Search
CPC ..... A61B 5/02233; A61B 5/023; A61B 5/742; A61B 5/681; A61B 5/022; A61B 2560/0214
See application file for complete search history.

(56) References Cited

U.S. PATENT DOCUMENTS

2003/0210149 A1* 11/2003 Reisman ................ G08B 21/22
340/573.4
2008/0059133 A1* 3/2008 Edwards ................ G06Q 10/00
703/7
(Continued)

FOREIGN PATENT DOCUMENTS

JP   H09-101220 A   4/1997
JP   H11-299748 A   11/1999
(Continued)

OTHER PUBLICATIONS

The English-language machine translation of WO 2013168345 A1 is provided herewith.*
(Continued)

*Primary Examiner* — Navin Natnithithadha
*Assistant Examiner* — Andrey Shostak
(74) *Attorney, Agent, or Firm* — Osha Liang LLP

(57) ABSTRACT

A blood pressure meter includes a pump and a first fluid path provided inside a main body. The first fluid path feeds a fluid from the pump to a fluid bladder or discharges the fluid from the fluid bladder. A pressure sensor is mounted on a first substrate disposed inside the main body. A second fluid path that introduces the fluid from the fluid bladder to the pressure sensor is provided. The second fluid path includes an inlet pipe that is integrally formed with a sensor package that incorporates the pressure sensor, and extends straight between the fluid bladder and the pressure sensor. A second substrate on which a blood pressure measurement element is mounted is disposed in a space that is located between the first substrate and the fluid bladder in a thickness direction and is adjacent to the second fluid path in a planar direction.

18 Claims, 18 Drawing Sheets

(51) Int. Cl.
*A61B 5/00* (2006.01)
*A61B 5/023* (2006.01)

(52) U.S. Cl.
CPC .............. *A61B 5/681* (2013.01); *A61B 5/742* (2013.01); *A61B 2560/0214* (2013.01)

(56) References Cited

U.S. PATENT DOCUMENTS

| | | |
|---|---|---|
| 2008/0228089 A1 | 9/2008 | Cho et al. |
| 2015/0025400 A1* | 1/2015 | Nishioka ................ A61B 5/022 600/499 |
| 2016/0206215 A1* | 7/2016 | Takahashi .............. A61B 5/681 |

FOREIGN PATENT DOCUMENTS

| | | | |
|---|---|---|---|
| JP | 2006-158543 A | 6/2006 | |
| JP | 2010-057628 A | 3/2010 | |
| JP | 2012-152520 A | 8/2012 | |
| JP | 2013-220187 A | 10/2013 | |
| JP | 2013-236657 A | 11/2013 | |
| JP | WO 2013168345 A1 * | 11/2013 | ............. A61B 5/022 |
| JP | 2014-033829 A | 2/2014 | |
| WO | 2012/014614 A1 | 2/2012 | |

OTHER PUBLICATIONS

International Search Report issued in PCT/JP2017/019568, dated Aug. 1, 2017 (2 pages).
Written Opinion issued in PCT/JP2017/019568, dated Aug. 1, 2017 (3 pages).
Decision to Grant a Patent issued in Japanese Application No. 2016-133563, dated Jun. 6, 2017 (6 pages).

* cited by examiner

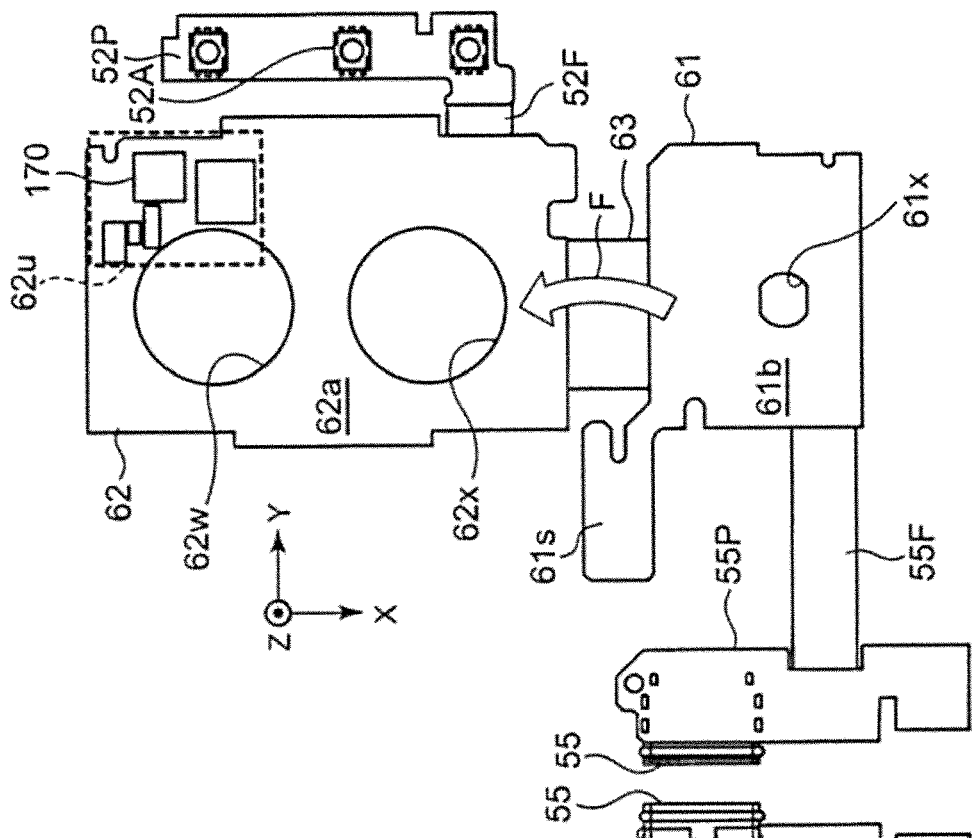
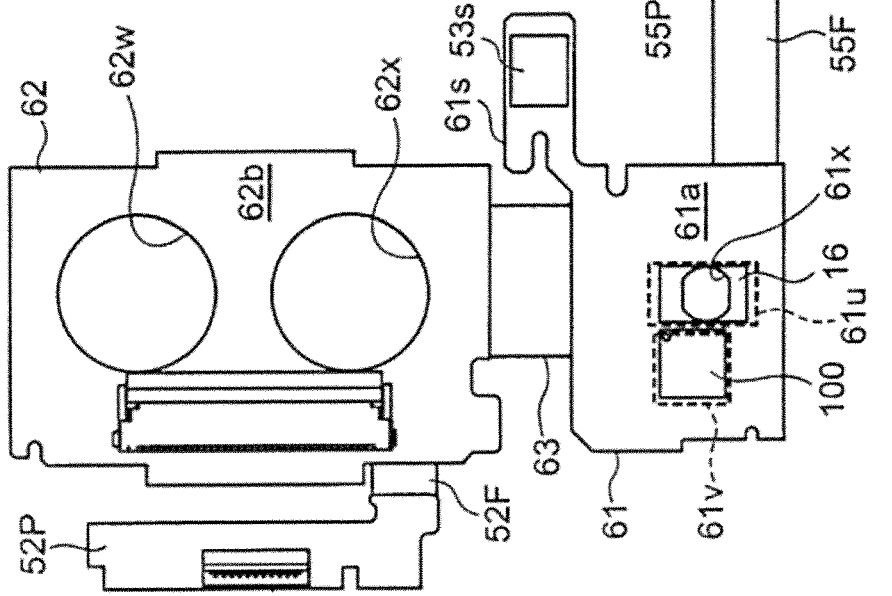
FIG. 16A
FIG. 16B

BLOOD PRESSURE METER

TECHNICAL FIELD

The present invention relates to a blood pressure meter. More specifically, the invention relates to an electronic blood pressure meter that detects the pressure of a fluid supplied to a blood pressure measurement cuff by using a pressure sensor through an inlet pipe that is in communication with the cuff and obtains a blood pressure value based on the detected pressure.

BACKGROUND ART

As this type of blood pressure meter, for example, a blood pressure meter as disclosed in Patent Document 1 (JP H09-101220A) is known that includes a pressure sensor module including a tubular inlet pipe integrally formed on a bottom surface of a package incorporating a pressure sensor so as to protrude from the bottom surface. The pressure sensor module package is attached onto an upper surface of a circuit substrate, with the inlet pipe extending down to the circuit substrate through a through hole formed in advance in the circuit substrate. The inlet pipe is connected to a cuff via an elongated tube (connecting pipe).

Also, for recent blood pressure meters, in particular, wrist-worn blood pressure meters, there is a growing need to produce miniaturized products. For example, Patent Document 2 (JP 2013-220187A) discloses a wrist-worn blood pressure meter in which a fluid bladder enclosed in a blood pressure measurement cuff and a pressure sensor are disposed in a stacked manner in a thickness direction, with a fluid path (corresponding to the inlet pipe described above) being provided in a straight manner between the fluid bladder and the pressure sensor. With this configuration, a miniaturized and thinner product is achieved.

CITATION LIST

Patent Literature

Patent Document 1: JP H09-101220A
Patent Document 2: JP 2013-220187A

SUMMARY OF INVENTION

However, with the blood pressure meters disclosed in Patent Document 1 (JP H09-101220A) and Patent Document 2 (JP 2013-220187A), there is a relatively large space around the inlet pipe (or the fluid path) in which a component is not disposed. Accordingly, there is a possibility that miniaturization of a product, in particular, miniaturization in a planar direction can be further promoted by effectively using the space.

Thus, one or more embodiments of the present invention provide a blood pressure meter that can promote miniaturization of a product, in particular, miniaturization in a planar direction.

A blood pressure meter according to one or more embodiments of the present invention is a blood pressure meter that is worn wrapped around a measurement area, the blood pressure meter including: a strip-shaped belt that includes a fluid bladder to which a fluid is supplied, and is wrapped around the measurement area; a main body that is provided on an outer surface side of the belt; a pump that is provided inside the main body, and is capable of supplying the fluid to the fluid bladder; a first fluid path that feeds the fluid from the pump to the fluid bladder or discharges the fluid from the fluid bladder; a pressure sensor that is incorporated in a sensor package and mounted on a first substrate disposed inside the main body, and is capable of detecting the pressure in the fluid bladder; and a second fluid path that introduces the fluid from the fluid bladder to the pressure sensor, wherein the second fluid path includes an inlet pipe that is integrally formed with the sensor package as a circumferential wall of the second fluid path, and extends straight between the fluid bladder and the pressure sensor, and a second substrate on which a blood pressure measurement element is mounted is disposed in a space that is located between the first substrate and the fluid bladder in a thickness direction and is adjacent to the second fluid path in a planar direction perpendicular to the thickness direction.

In this specification, the term "outer surface" of the strip-shaped belt refers to a surface that is distant from the measurement area.

Also, the expression "the second fluid path . . . extends straight" means that the second fluid path extends straight so as to include a fluid inlet port of the sensor package and a fluid inlet/outlet port of the fluid bladder in a state in which the sensor package and the fluid bladder are disposed to oppose each other in the thickness direction.

Also, the term "thickness direction" refers to a direction vertical to an outer circumferential surface of the measurement area, or in other words, a direction through the strip-shaped belt. The term "planar direction" refers to a direction in which a surface perpendicular to the thickness direction extends.

Also, the expression "space that is adjacent to the second fluid path in the planar direction" refers to, for example, the entire area around the second fluid path, or may refer to a space that is on one side of the second fluid path.

Also, the term "blood pressure measurement element" encompasses, for example, a pump driving circuit for driving the pump, and the like.

In the blood pressure meter according to one or more embodiments of the present invention, the fluid is fed from the pump provided inside the main body to the fluid bladder through the first fluid path or discharged from the fluid bladder. With this configuration, the pressure in the fluid bladder is increased or decreased. Also, the pressure of the fluid supplied to the fluid bladder is detected by the pressure sensor (mounted on the first substrate) through the second fluid path. Based on the detected pressure, blood pressure values are obtained by using, for example, a known oscillometric method. Here, in the blood pressure meter, a second substrate on which a blood pressure measurement element is mounted is disposed in a space that is located between the first substrate and the fluid bladder in a thickness direction and is adjacent to the second fluid path in a planar direction perpendicular to the thickness direction. Accordingly, the space that is adjacent to the second fluid path can be effectively used by the second substrate. As a result, it is possible to promote miniaturization of the product, in particular, miniaturization in the planar direction.

To be specific, if a configuration is applied in which the blood pressure measurement element that needs to be mounted on the second substrate is mounted on the first substrate in the absence of the second substrate, there is no option but to increase the dimension of the first substrate in the planar direction accordingly (by an amount corresponding to the increased region where the blood pressure measurement element is disposed). However, with the blood pressure meter according to one or more embodiments of the present invention, the space where a component is not disposed in a conventional blood pressure meter can be effectively used by the second substrate. As a result, the dimension of the first substrate in the planar direction can be reduced, and miniaturization in the planar direction can be promoted.

With the blood pressure meter according to the embodiment, the second substrate includes an escaping portion for allowing the second fluid path to pass therethrough in a plane surface extending along the planar direction.

The "escaping portion" formed in the second substrate may be a through hole extending through the substrate in the thickness direction, or may be a cut-out portion formed in a peripheral edge of the plane surface.

With the blood pressure meter according to the embodiment, the second substrate includes an escaping portion for allowing the second fluid path to pass therethrough in a plane surface extending along the planar direction. Accordingly, the second substrate does not interfere with the second fluid path.

With the blood pressure meter according to the embodiment, the pump is disposed at a position adjacent to the first substrate in the planar direction, the first fluid path includes an outlet pipe of the pump as a circumferential wall of the first fluid path, and extends straight between the pump and the fluid bladder in parallel to the second fluid path, and the second substrate extends in a space that is located between the pump and the fluid bladder in the thickness direction and is adjacent to the first fluid path in the planar direction.

In this specification, the expression "the first fluid path . . . extends straight" means that the first fluid path extends straight so as to include a fluid outlet port of the pump and a fluid inlet/outlet port of the fluid bladder in a state in which the pump and the fluid bladder are disposed opposing each other in the thickness direction.

With the blood pressure meter according to the embodiment, the second substrate extends in a space that is located between the pump and the fluid bladder in the thickness direction and is adjacent to the first fluid path in the planar direction. Accordingly, the space that is adjacent to the first fluid path can be effectively used by the second substrate. As a result, miniaturization of the product can be further promoted.

With the blood pressure meter according to the embodiment, the second substrate includes another escaping portion for allowing the first fluid path to pass therethrough in the plane surface extending along the planar direction.

With the blood pressure meter according to the embodiment, the second substrate includes another escaping portion for allowing the first fluid path to pass therethrough in the plane surface extending along the planar direction. Accordingly, the second substrate does not interfere with the first fluid path.

With the blood pressure meter according to the embodiment, a pump driving circuit for driving the pump is mounted on the second substrate, a region of the second substrate in which the pump driving circuit is mounted is provided to be spaced apart, in the planar direction, from a region of the first substrate in which the pressure sensor is mounted and to oppose the pump, and a lead wire that electrically connects the pump driving circuit and the pump is connected to an end portion of the pump, the end portion being on an opposite side of the pressure sensor in the planar direction.

With the blood pressure meter according to the embodiment, a region of the second substrate in which the pump driving circuit is mounted is provided to be spaced apart, in the planar direction, from a region of the first substrate in which the pressure sensor is mounted and to oppose the pump. Also, a lead wire that electrically connects the pump driving circuit and the pump is connected to an end portion of the pump, the end portion being on an opposite side of the pressure sensor in the planar direction. Accordingly, heat generated in the pump driving circuit and the lead wire during driving of the pump is unlikely to be transferred to the pressure sensor. As a result, the output of the pressure sensor is unlikely to be affected by the generated heat, and the accuracy of blood pressure measurement is enhanced.

With the blood pressure meter according to the embodiment, a control unit that receives an output of the pressure sensor and performs blood pressure calculation processing is mounted on the first substrate, and a region of the first substrate in which the control unit is mounted is provided adjacent to a region of the first substrate in which the pressure sensor is mounted.

With the blood pressure meter according to the embodiment, in the first substrate, a region in which the control unit is mounted is provided adjacent to the region in which the pressure sensor is mounted. Accordingly, the interconnect between the pressure sensor and the control unit is relatively short, which makes it unlikely that noise will be included in the output of the pressure sensor. As a result, the accuracy of blood pressure measurement is further enhanced.

With the blood pressure meter according to the embodiment, at least the region of the first substrate in which the pressure sensor is mounted and the region of the first substrate in which the control unit is mounted are shielded, in the thickness direction, by a display device including a metal plate that is disposed extending outward of the first substrate and the second substrate that is disposed extending inward of the first substrate.

The expression "outward of the first substrate" refers to a side that is distant from the measurement area. Likewise, the expression "inward of the first substrate" refers to a side close to the measurement area.

With the blood pressure meter according to the embodiment, at least the region of the first substrate in which the pressure sensor is mounted and the region of the first substrate in which the control unit is mounted are shielded, in the thickness direction, by a display device including a metal plate that is disposed extending outward of the first substrate and the second substrate that is disposed extending inward of the first substrate. Accordingly, this makes it unlikely that noise will be included in the output of the pressure sensor. As a result, the accuracy of blood pressure measurement is further enhanced.

With the blood pressure meter according to the embodiment, the main body includes a bottom wall between the second substrate and the fluid bladder, the bottom wall including a through cylindrical portion extending in the thickness direction so as to constitute a portion of the circumferential wall of the second fluid path, and the inlet pipe of the pressure sensor and a nipple that is in communication with the fluid bladder are hermetically attached to the cylindrical portion of the bottom wall.

With the blood pressure meter according to the embodiment, the inlet pipe of the pressure sensor and a nipple that is in communication with the fluid bladder are hermetically attached to the cylindrical portion of the bottom wall. The second fluid path is thereby constituted. Here, if a configuration is applied in which the inlet pipe of the pressure sensor and the nipple that is in communication with the fluid bladder can be directly fitted and attached, stress may be applied to the pressure sensor from the nipple via the inlet pipe and the sensor package during assembly, which may compromise the characteristics of the pressure sensor. However, with the blood pressure meter according to the embodiment, the inlet pipe of the pressure sensor and the nipple that is in communication with the fluid bladder are hermetically attached to the cylindrical portion of the bottom wall. Accordingly, it is possible to independently perform an operation to attach the inlet pipe of the pressure sensor to the cylindrical portion of the bottom wall and an operation to attach the nipple that is in communication with the fluid bladder to the cylindrical portion of the bottom wall. Thus, there is no possibility that the characteristics of the pressure sensor will be compromised due to the application of stress from the nipple during assembly. As a result, the reliability of assembly is enhanced.

With the blood pressure meter according to the embodiment, a battery for supplying power to each constituent element of the blood pressure meter is mounted inside the main body, and the battery continuously occupies a range in which at least the first substrate and the second substrate are disposed in the thickness direction.

With the blood pressure meter according to the embodiment, the battery continuously occupies a range in which at least the first substrate and the second substrate are disposed in the thickness direction. Accordingly, the dimension in the thickness direction of the battery can be configured to be relatively large. As a result, it is possible to increase the battery capacity.

With the blood pressure meter according to the embodiment, the first substrate, the pump, the second substrate, and the battery form a rectangular parallelepipedal shaped outer contour as a whole.

With the blood pressure meter according to the embodiment, the first substrate, the pump, the second substrate, and the battery form a rectangular parallelepipedal shaped outer contour as a whole. That is, these elements are assembled in a compact design. As a result, miniaturization of the product is further promoted.

As is evident from the above description, with the blood pressure meter according to one or more embodiments of the present invention, it is possible to promote miniaturization of the product, in particular, miniaturization in the planar direction.

BRIEF DESCRIPTION OF DRAWINGS

FIG. 16(A) is a diagram showing, in a laid-out state, an upper substrate 61 and a lower substrate 62 that are connected to each other by an FPC cable 63 before the blood pressure meter 1 is assembled, and shows an upper surface 61a of the upper substrate 61 and a lower surface 62b of the lower substrate 62, so as to realize hermetic sealing.

FIG. 16(B) is a diagram showing, in a laid-out state, the upper substrate 61 and the lower substrate 62 that are connected to each other by the FPC cable 63 before the blood pressure meter 1 is assembled, and corresponds to the back side of FIG. 16(A).

DESCRIPTION OF EMBODIMENTS

Figure 1A:
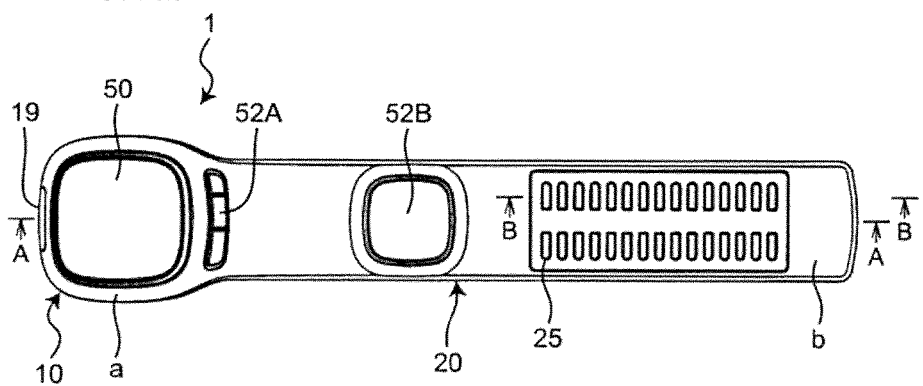
FIG. 1A is a top view showing an external appearance of a blood pressure meter 1 according to an embodiment of the present invention.

Hereinafter, an embodiment of the present invention will be described in detail with reference to the drawings. In the embodiment given below, the same constituent elements are given the same reference numerals and a description thereof is omitted.

Figure 1B:
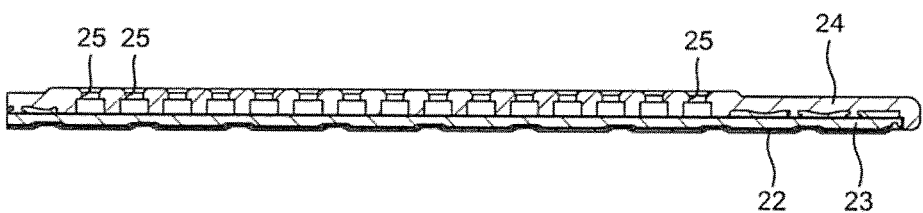
FIG. 1B is a vertical cross-sectional view of the blood pressure meter 1 taken along the line B-B shown in FIG. 1A.
Figure 1C:
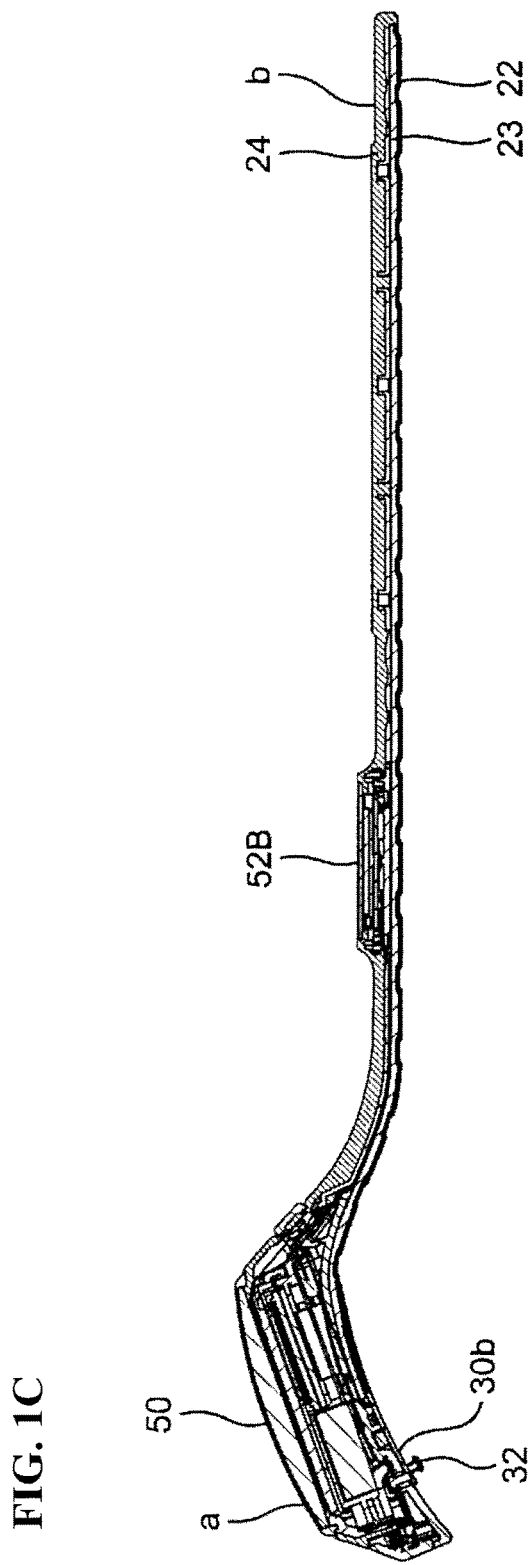
FIG. 1C is a vertical cross-sectional view of the blood pressure meter 1 taken along the line A-A shown in FIG. 1A.
Figure 2:
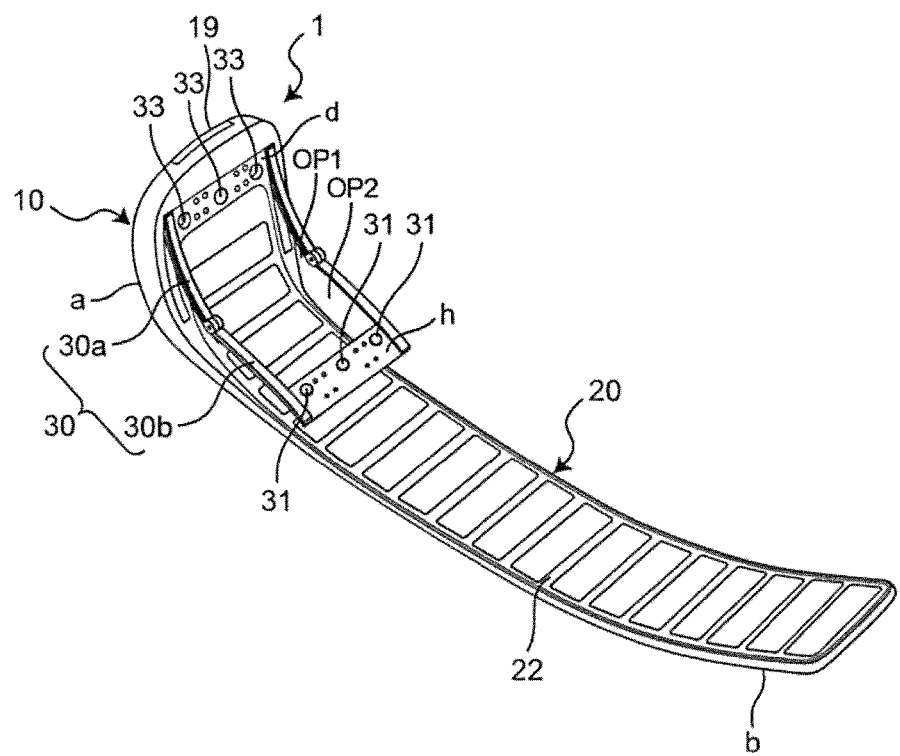
FIG. 2 is a bottom view of the blood pressure meter 1 shown in FIG. 1.
Figure 3:
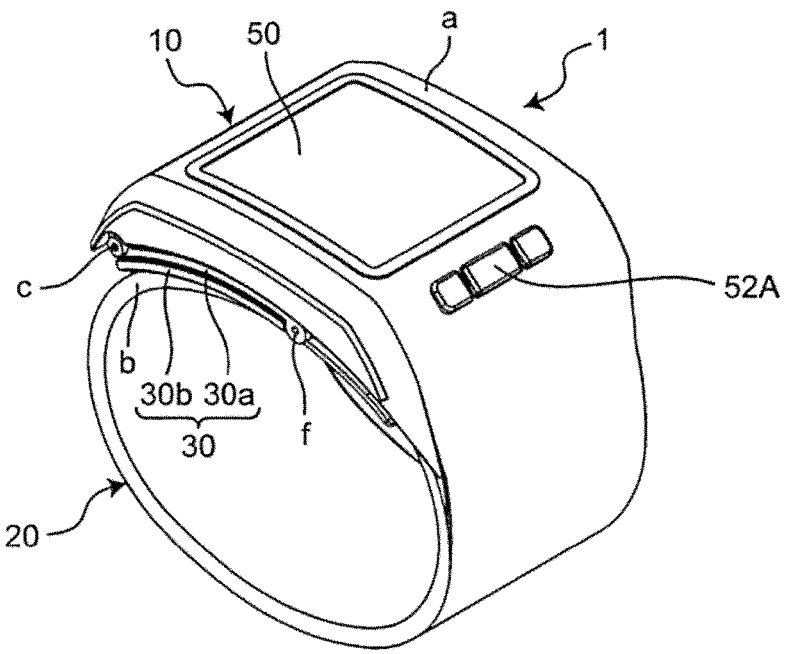
FIG. 3 is a perspective view of the blood pressure meter 1 shown in FIG. 1 when it is formed into a loop.
Figure 4:
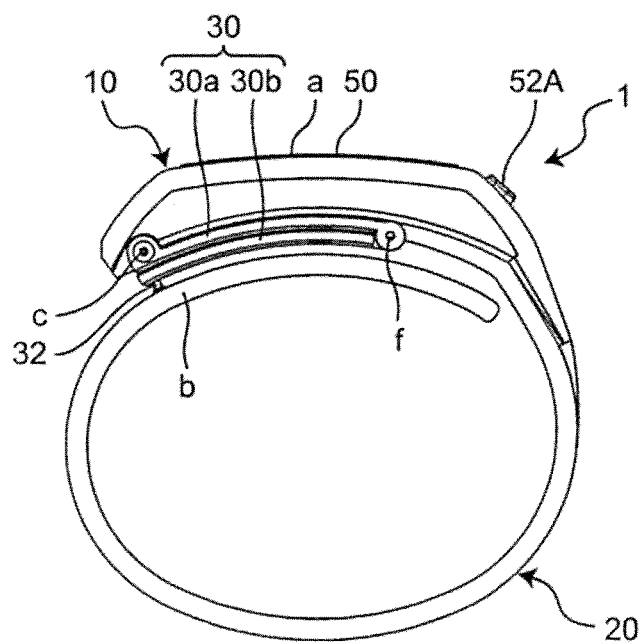
FIG. 4 is a diagram illustrating the blood pressure meter 1 shown in FIG. 3 as viewed from a direction vertical to the loop of the belt.
Figure 5:
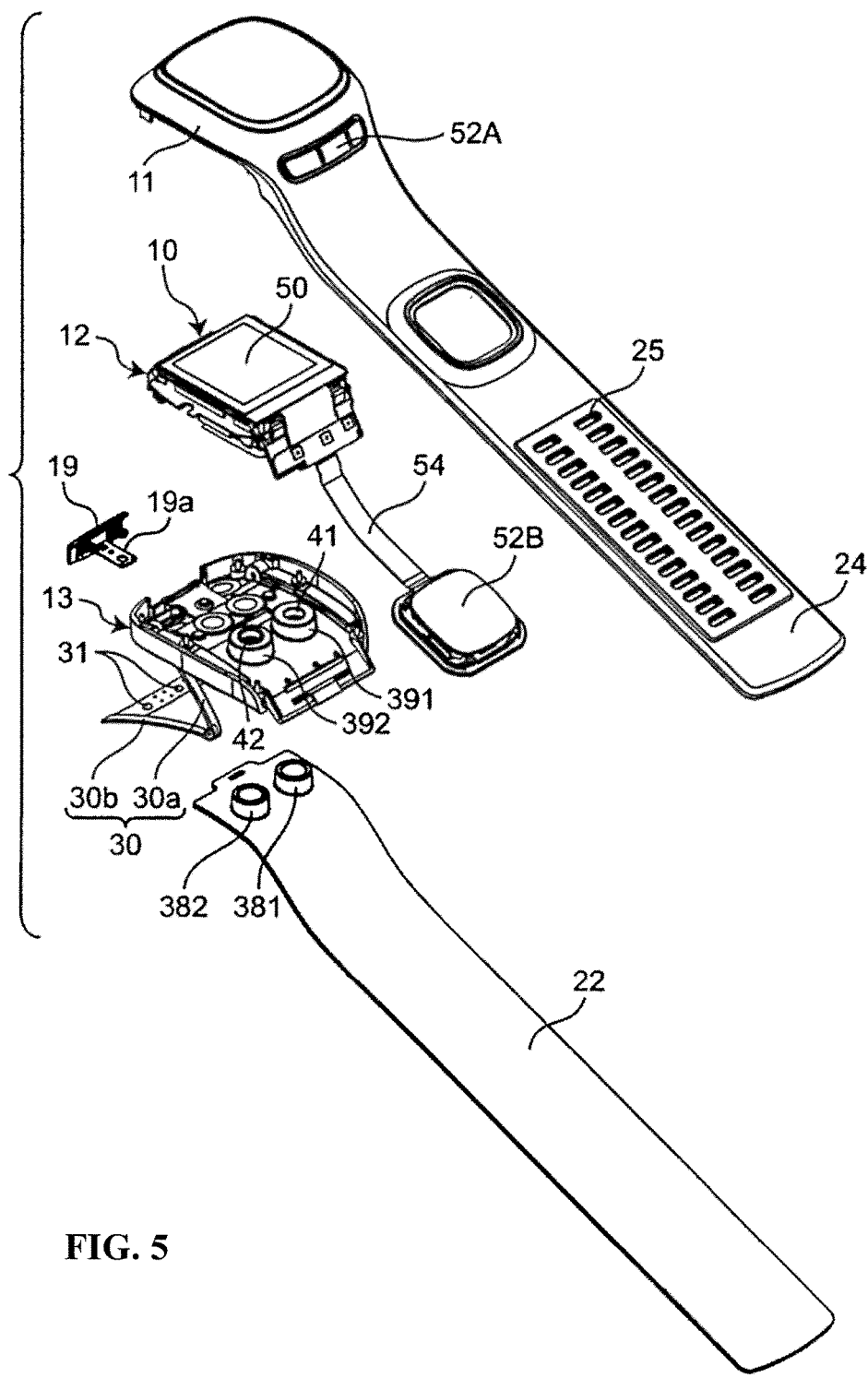
FIG. 5 is an exploded perspective view illustrating a structure of the blood pressure meter 1 shown in FIG. 1A.

FIG. 1A is a top view showing an external appearance of a blood pressure meter 1 according to an embodiment of the present invention. FIG. 1B is a vertical cross-sectional view of the blood pressure meter 1 taken along the line B-B shown in FIG. 1A. FIG. 1C is a vertical cross-sectional view of the blood pressure meter 1 taken along the line A-A shown in FIG. 1A. FIG. 2 is a bottom view of the blood pressure meter 1 shown in FIG. 1. FIG. 3 is a perspective view of the blood pressure meter 1 shown in FIG. 1 when the blood pressure meter 1 is worn wrapped around a measurement area. FIG. 4 is a diagram illustrating the blood pressure meter 1 shown in FIG. 3 as viewed from a direction vertical to the loop of the belt. FIG. 5 is an exploded perspective view illustrating a structure of the blood pressure meter 1 shown in FIG. 1A.

Figure 7A:
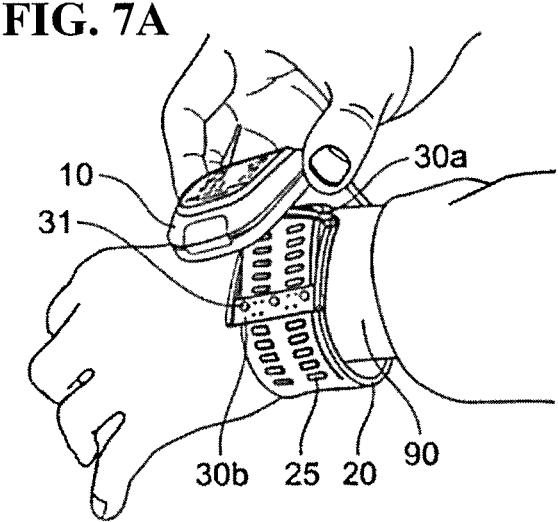
FIG. 7A is a schematic diagram illustrating a first procedure of wearing the blood pressure meter 1 shown in FIG. 1 on a wrist and performing measurement.
Figure 7B:
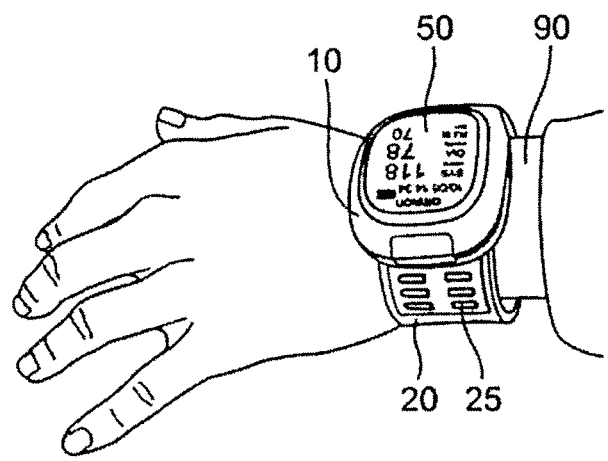
FIG. 7B is a schematic diagram illustrating a second procedure of wearing the blood pressure meter 1 shown in FIG. 1 on the wrist and performing measurement.
Figure 7C:
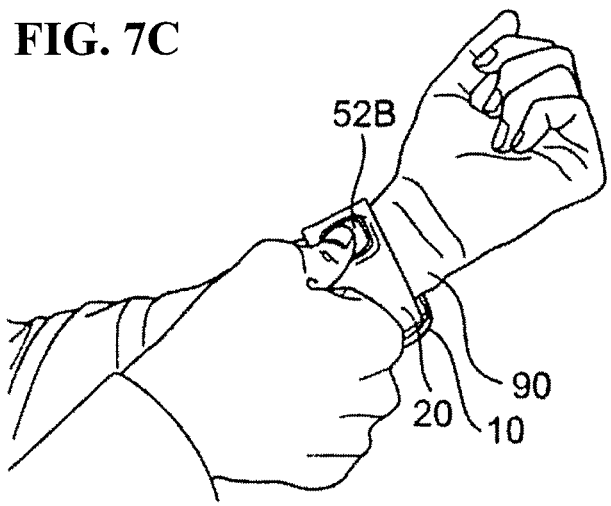
FIG. 7C is a schematic diagram illustrating a third procedure of wearing the blood pressure meter 1 shown in FIG. 1 on the wrist and performing measurement.

As can be seen from FIG. 3, the blood pressure meter 1 is worn wrapped around a rod-shaped measurement area such as, for example, a user's wrist 90 (see FIGS. 7A to 7C). The blood pressure meter 1 includes a strip-shaped belt 20 that is wrapped around the measurement area, a main body 10 that is disposed in a base end portion a in a lengthwise direction of the belt 20 on an outer surface side of the belt 20 and includes a blood pressure measurement element, and a buckle 30 for joining the base end portion a and a lead end portion b that is provided on the opposite side of the base end portion a in the lengthwise direction of the belt 20 such that the belt 20 forms a loop. Here, the belt 20 functions as a blood pressure measurement cuff. Hereinafter, a structure of the belt 20 will be described.

As can be seen from FIG. 1B, the belt 20 includes a fluid bladder 22 for compressing the measurement area when measuring blood pressure, a reinforcing layer 23 that is provided along an outer surface of the fluid bladder 22 and is for suppressing outward inflation of the fluid bladder 22, and an outer circumferential layer 24 that is provided along an outer surface of the reinforcing layer 23 so as to cover the reinforcing layer 23. Accordingly, because outward inflation of the fluid bladder 22 can be suppressed, it is possible to improve the efficiency of compressing the measurement area and further enhance the accuracy of blood pressure measurement. On the other hand, a surface of the fluid bladder 22 (the surface serving as an inner surface when worn) has a plurality of irregularities along the lengthwise direction so as to facilitate inflation toward the measurement area.

The reinforcing layer 23 is the hardest, followed by the outer circumferential layer 24 and then the fluid bladder 22. Accordingly, the reinforcing layer 23 suppresses outward inflation of the fluid bladder 22 when the fluid bladder 22 is inflated, and thus the efficiency of compressing the measurement area can be improved. Accordingly, the accuracy of blood pressure measurement can be further enhanced. Furthermore, the outer circumferential layer 24 that is not as hard as the reinforcing layer 23 covers an outer circumference of the reinforcing layer 23, and thus feels soft when the user touches the outer circumferential layer 24 of the belt 20 with his/her hand.

As can be clearly seen from FIGS. 1A, 1B, and 3, an operation unit including a blood pressure measurement switch 52B for inputting an instruction to perform a biometric information measurement is disposed in an area (a substantially center portion in this example) that is different from a specific portion (the base end portion a in this example) in which the main body 10 is disposed in the lengthwise direction on the outer surface side of the belt 20. Also, as shown in FIG. 5, the main body 10 includes a frame-shaped upper housing 11, a lower housing 13 that is combined with the upper housing 11, and a main body assembly 12 that is housed between the upper housing 11 and the lower housing 13. The main body assembly 12 includes a display device 50 that is fitted into the frame of the upper housing 11. A FPC (flexible printed circuit) cable 54 for electrically connecting the main body 10 and the operation unit 5 is provided between the fluid bladder 22 and the reinforcing layer 23. Because the main body 10 and the operation unit 52 are electrically connected by the FPC cable 54 as described above, the belt 20 can be configured to be thin. In the present embodiment, only the operation unit is disposed, but the present invention is not limited thereto, and it is also possible to dispose a communication unit and a display unit. so as to realize hermetic sealing As can be seen from FIG. 2, magnets 33 are provided on an inner surface side of the base end portion a of the belt 20, and metal projection portions 31 that are attracted to the magnets 33 are provided on a second plate frame member 30b, thereby constituting an attraction mechanism. With this attraction mechanism, the inner surface side of the base end portion a of the belt 20 or one end portion d of a first plate frame member 30a and another end portion h of the second plate frame member 30b are attracted to each other. Accordingly, when the main body 10 and the first plate frame member 30a and the second plate frame member 30b of the buckle 30 are folded, an inner surface of the main body 10 and the first plate frame member 30a and the second plate frame member 30b of the buckle 30 are guided to overlap each other.

In addition to or instead of the attraction mechanism, it is desirable to provide a lock mechanism that engages the inner surface side of the base end portion a of the belt 20 or the one end portion d of the first plate frame member 30a with the other end portion h of the second plate frame member 30b. It is also desirable that the attraction mechanism and/or the lock mechanism include/includes an unlock mechanism for releasing the attraction and/or the engagement. In this example, a release button 19 (see FIGS. 1A, 2, and 5) for canceling attraction is provided in the main body 10 as the unlock mechanism. As shown in FIG. 5, the release button 19 is integrally formed with a slide plate 19a. In response to the release button 19 being pressed toward the inside of the main body 10, the slide plate 19a is inserted between the one end portion d of the first plate frame member 30a and the other end portion h of the second plate frame member 30b shown in FIG. 6B like a wedge so as to cancel the attraction between the first plate frame member 30a and the second plate frame member 30b.

Figure 6A:
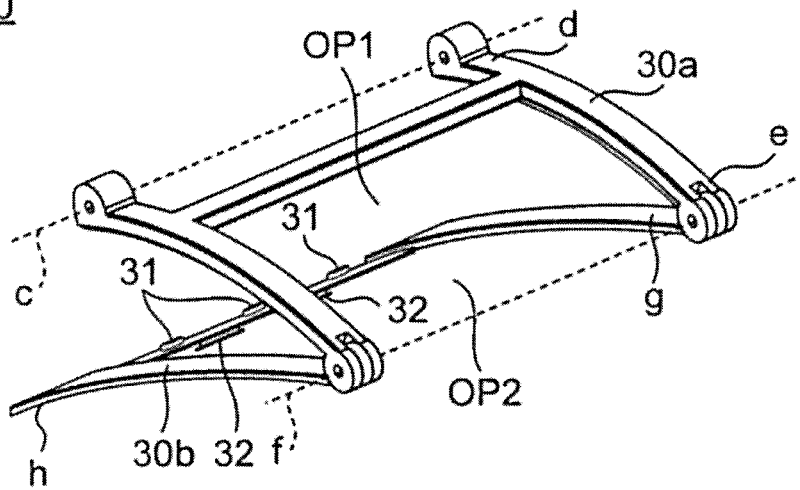
FIG. 6A is a schematic perspective view illustrating a first state during operation of a buckle 30 shown in FIG. 5.
Figure 6B:
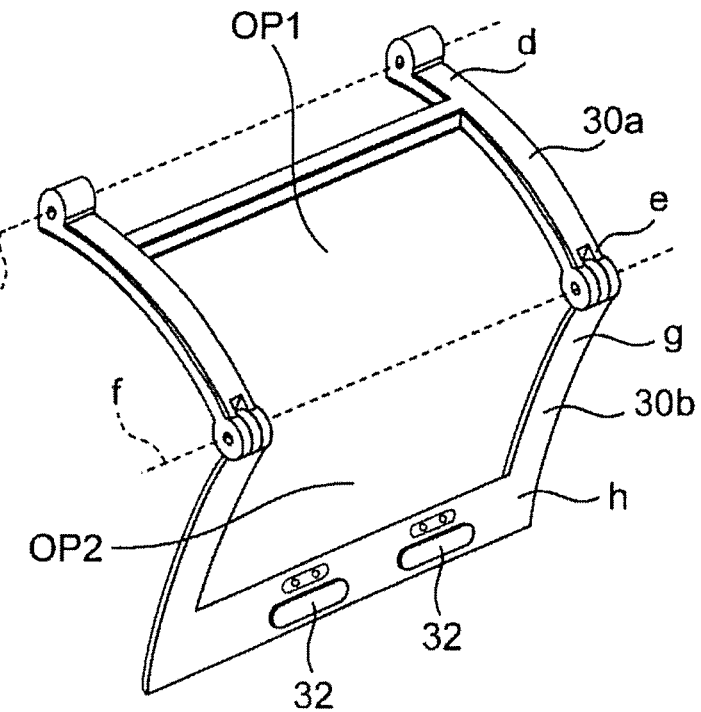
FIG. 6B is a schematic perspective view illustrating a second state during operation of the buckle 30 shown in FIG. 5.

As shown in FIGS. 6A and 6B, a first fixing element including engaging portions 32 having a projection shape is provided on an inner surface of the other end portion h of the second plate frame member 30b, and also as shown in FIGS. 1A, 1B, and 5, a second fixing element including engaged portions 25 having a recessed shape that can be engaged with the engaging portions 32 is provided on an outer surface of the lead end portion b of the belt 20. With this configuration, as shown in FIGS. 3 and 4, the belt 20 can be formed into a loop by engaging the second plate frame member 30b with the lead end portion b of the belt 20. Accordingly, the blood pressure meter 1 can be fixed to the measurement area. Furthermore, the second fixing element (the engaged portions 25) that has a non-through recessed shape and is configured to be capable of engaging with the first fixing element (the engaging portions 32) having a projection shape is provided on the outer surface of the lead end portion b of the belt 20, and thus these fixing elements do not interfere with the fluid bladder 22. Accordingly, the wrist 90 that serves as the measurement area can be reliably compressed by the fluid bladder 22 while the blood pressure is being measured.

The present embodiment is configured such that the first fixing element having a projection shape and the second fixing element having a recessed shape are used, but the present invention is not limited to this configuration. It is possible to, for example, use a first fixing element having a recessed shape and a second fixing element having a projection shape. In this case as well, the same effects of the present embodiment can be obtained.

As can be clearly seen from FIGS. 1A, 1B, and 5, a plurality of engaged portions 25 are formed side by side along the lengthwise direction of the belt 20 such that the attachment position of the other end portion h of the second plate frame member 30b can be adjusted in the lengthwise direction of the belt 20. Accordingly, it is possible to adjust the attachment position of the other end portion h (see FIG. 6B) of the second plate frame member 30b in the lengthwise direction of the belt 20. With this configuration, the length of the loop of the belt 20 can be variably set so as to fit snug to the circumferential length of the wrist 90 that serves as the measurement area.

The engaged portions 25 are also arranged in a plurality of (two in this example) rows along a width direction of the belt 20. Accordingly, even if the belt 20 is slightly twisted, the engagement between the engaging portions 32 and the engaged portions 25 is unlikely to be canceled.

Also, at least the outer surface of the lead end portion b of the belt 20 is made of a flexible material. Accordingly, the engagement of the engaging portions 32 and the engaged portions 25 can be easily disengaged. It is also possible to provide a detachment mechanism (not shown) that allows the user to cancel the engagement between the engaging portions 32 and the engaged portions 25. In this case, with the detachment mechanism, the user can cancel the engagement between the engaging portions 32 and the engaged portions 25 while the belt 20 is wrapped around the wrist 90. Accordingly, the belt 20 can be more easily detached.

FIG. 6A is a schematic perspective view illustrating a first state during operation of the buckle 30 shown in FIG. 5, and FIG. 6B is a schematic perspective view illustrating a second state during operation of the buckle 30 shown in FIG. 5.

The buckle 30 includes, on the inner surface side of the base end portion a of the belt 20, the first plate frame member 30a that is attached to the one end portion d so as to be capable of pivoting about an axis c that intersects the lengthwise direction of the belt 20. The first plate frame member 30a extends, in a curved form, from the one end portion d to another end portion e that is on the opposite side. The buckle 30 also includes, on the other end portion e of the first plate frame member 30a, the second plate frame member 30b that is attached to one end portion g so as to be capable of pivoting about an axis f that is parallel to the axis c. The second plate frame member 30b extends, in a curved form, from the one end portion g to the other end portion h that is on the opposite side.

Furthermore, the other end portion h of the second plate frame member 30b is configured to be capable of being attached to the lead end portion b of the belt 20, and the first plate frame member 30a and the second plate frame member 30b respectively have a first opening portion OP1 and a second opening portion OP2 that extend through their plane surfaces. Here, the first opening portion OP1 of the first plate frame member 30a and the second opening portion OP2 of the second plate frame member 30b are configured to be continuous in the thickness direction of the main body 10 when the inner surface of the main body 10 and the first plate frame member 30a and the second plate frame member 30b of the buckle 30 are folded so as to overlap each other.

Accordingly, it is possible to implement a configuration in which the fluid bladder 22 is disposed on the inner side of the main body 10 so as to compress the measurement area.

The first opening portion OP1 is open toward the other end portion e of the first plate frame member 30a, and the second opening portion OP2 is open toward the one end portion g of the second plate frame member 30b. Accordingly, the first opening portion OP1 and the second opening portion OP2 are in communication with each other. That is, the first plate frame member 30a and the second plate frame member 30b are formed to have a substantially angular U shape and are joined to each other on the side on which their opening portions are open. Also, as can be clearly seen from FIG. 2, the fluid bladder 22 for compressing the measurement area during blood pressure measurement is provided along the lengthwise direction of the belt 20 in the belt 20, and the fluid bladder 22 is in communication with the inside of the main body 10 through a region corresponding to the first opening portion OP1 and the second opening portion OP2 in a folded state.

With this configuration, the fluid bladder 22 can compress a spatially continuous region of the wrist 90 that serves as the measurement area in a circumferential direction thereof, the spatially continuous region extending from a portion corresponding to the inside of the main body 10 toward the lead end portion b of the belt 20. Accordingly, the contact area between the fluid bladder 22 and the measurement area can be increased, and it is therefore possible to improve the efficiency of compressing the arteries. Accordingly, the accuracy of blood pressure measurement can be further enhanced.

Also, the fluid bladder 22 extends to the lead end portion b of the belt 20 along the lengthwise direction. When the inner surface of the main body 10 and the first plate frame member 30a and the second plate frame member 30b of the buckle 30 are folded so as to overlap each other, a portion of the main body 10 that is in communication with the fluid bladder 22 overlaps a portion to which the fluid bladder 22 of the belt 20 extends.

With this configuration, the overlapping region of the belt 20 in the lengthwise direction has a thickness thicker than that of the other region of the main body 10 and thus is inflated by an amount corresponding to the thickness. Accordingly, an excessive amount of pressure applied to compress the arteries is reduced as a result of reducing the distance by which the arteries running through the wrist 90 escape due to being pressed by a region other than the overlapping region. As a result, the blood pressure values measured through the application of pressure by the fluid bladder can be brought closer to true values, and thus the accuracy of measurement can be enhanced. The effect of reducing the excessive amount of pressure applied to compress the arteries is also obtained even when the first opening portion OP1 of the first plate frame member 30a and the second opening portion OP2 of the second plate frame member 30b in the buckle 30 are omitted.

FIGS. 7A to 7C are schematic diagrams illustrating a procedure of wearing the blood pressure meter 1 shown in FIG. 1 on the wrist and performing measurement. When actually wearing the blood pressure meter 1 on the wrist 90, as shown in FIG. 7A, the user first places the belt 20 around the wrist 90, with the main body 10 and the first plate frame member 30a and the second plate frame member 30b of the buckle 30 being open. Then, the user inserts the lead end portion b of the belt 20 through the second opening portion OP2 (see FIGS. 6A and 6B) of the second plate frame member 30b and engages the engaging portions 32 of the second plate frame member 30b with the engaged portions 25 that are provided on the lead end portion b of the belt 20. By doing so, the belt 20 is formed into a loop and the wrist 90 passes through the loop of the belt 20. In this way, the length of the loop of the belt 20 can be set so as to fit snug to the circumferential length of the wrist 90.

Next, as shown in FIG. 7B, the main body 10 is moved closer toward the wrist 90 such that the inner surface of the main body 10 and the first plate frame member 30a and the second plate frame member 30b of the buckle 30 are folded so as to overlap each other. Then, the projection portions 31 of the second plate frame member 30b are attracted by the magnets 33. The blood pressure meter 1 is thereby worn on the wrist 90. Next, blood pressure measurement starts in response to the user pressing the blood pressure measurement switch 52B as shown in FIG. 7C.

Figure 8:
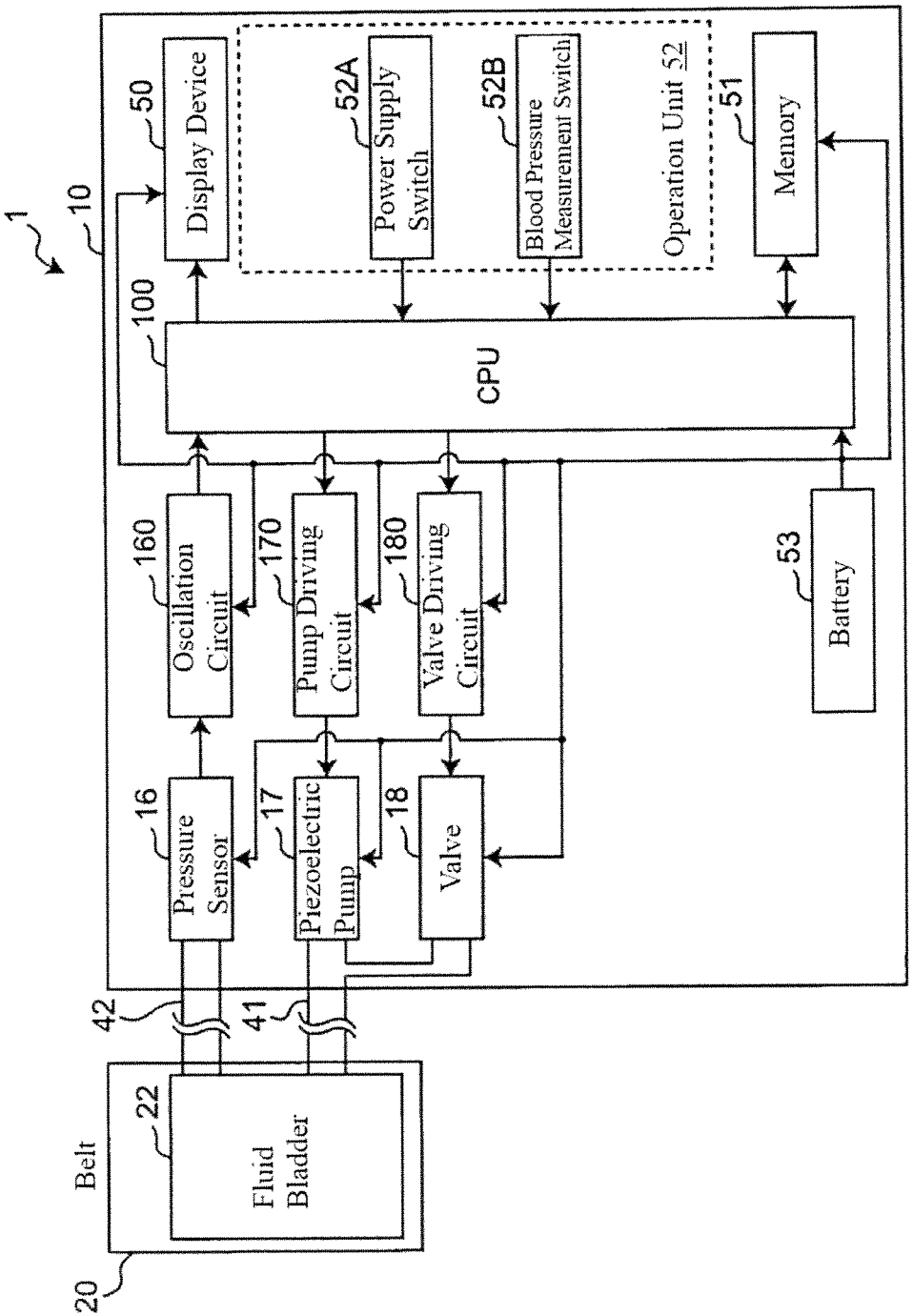
FIG. 8 is a block diagram schematically showing a configuration of a control system provided inside the blood pressure meter 1 shown in FIG. 1.

FIG. 8 is a block diagram schematically showing an internal configuration of the blood pressure meter 1 shown in FIG. 1. The main body 10 includes, in addition to the display device 50 and the operation unit 52 described above, a CPU (central processing unit) 100, a memory 51, a battery 53, a piezoresistive pressure sensor 16, a piezoelectric pump 17 that supplies air to the fluid bladder 22 as a fluid, a valve 18 for adjusting a discharge pressure (back pressure) of the piezoelectric pump 17, an oscillation circuit 160 that converts an output from the pressure sensor 16 to a frequency, a pump driving circuit 170 that drives the piezoelectric pump 17, and a valve driving circuit 180 that drives the valve 18. The piezoelectric pump 17 and the valve 18 are connected to the fluid bladder 22 enclosed in the belt 20 via a first fluid path 41, and the pressure sensor 16 is connected to the fluid bladder 22 enclosed in the belt 20 via a second fluid path 42. With this configuration, air flows between the piezoelectric pump 17 and the fluid bladder 22 and between the valve 18 and the fluid bladder 22 via the first fluid path 41. Also, air flows between the pressure sensor 16 and the fluid bladder 22 via the second fluid path 42.

The display device 50 includes a display, an indicator and the like, and displays predetermined information in accordance with a control signal from the CPU 100.

In the operation unit 52, a power supply switch 52A receives an instruction to turn on or off power supply from the battery 53. The blood pressure measurement switch 52B receives an instruction to start blood pressure measurement and an instruction to display data obtained through measuring blood pressure values, stored in the memory 51 on the display device 50. The switches 52A and 52B input an operation signal corresponding to a user's instruction to the CPU 100.

The memory 51 stores therein a program for controlling the blood pressure meter 1, settings data for setting various functions of the blood pressure meter 1, and data obtained as a result of measurement of blood pressure values. Also, the memory 51 is used a work memory during execution of a program.

In this example, the battery 53 is a secondary battery (lithium ion battery), and supplies power to the CPU 100, the pressure sensor 16, the piezoelectric pump 17, the valve 18, the display device 50, the memory 51, the oscillation circuit 160, the pump driving circuit 170, and the valve driving circuit 180. The battery 53 is configured to be rechargeable via a USB (Universal Serial Bus) terminal 55 (see, for example, FIG. 10B).

The CPU 100 functions as a control unit in accordance with the program for controlling the blood pressure meter 1 stored in the memory 51, and performs control for driving the piezoelectric pump 17 via the pump driving circuit 170 and driving the valve 18 via the valve driving circuit 180 in accordance with an operation signal from the operation unit 52. The valve 18 is opened or closed so as to control the pressure (cuff pressure) in the fluid bladder 22 by discharging or trapping air in the fluid bladder 22. Also, the CPU 100 calculates blood pressure values based on signals from the pressure sensor 16 and controls the display device 50 and the memory 51.

The piezoelectric pump 17 supplies air to the fluid bladder 22 via the first fluid path 41 so as to increase the pressure (cuff pressure) in the fluid bladder 22 enclosed in the belt 20. The valve 18 is opened or closed so as to control the cuff pressure by discharging the air in the fluid bladder 22 via the first fluid path 41 or trapping air in the fluid bladder 22. The pump driving circuit 170 drives the piezoelectric pump 17 based on a control signal provided from the CPU 100. The valve driving circuit 180 opens or closes the valve 18 based on a control signal provided from the CPU 100.

The pressure sensor 16 and the oscillation circuit 160 operate as a pressure detection unit that detects the cuff pressure. The pressure sensor 16 is, for example, a piezoresistive pressure sensor, and introduces air from the fluid bladder 22 via the second fluid path 42 and detects the pressure of the introduced air as the cuff pressure. In this example, the oscillation circuit 160 oscillates based on an electric signal value that is based on a change in electric resistance due to piezoresistance effect from the pressure sensor 16, and outputs a frequency signal having a frequency corresponding to the electric signal value of the pressure sensor 16 to the CPU 100. In this example, it is assumed that the oscillation circuit 160 is included in the CPU 100, and the function of the oscillation circuit 160 is implemented by a program executed by the CPU 100.

Hereinafter, a description will be given of operations performed by the blood pressure meter 1 configured as described above.

Figure 9:
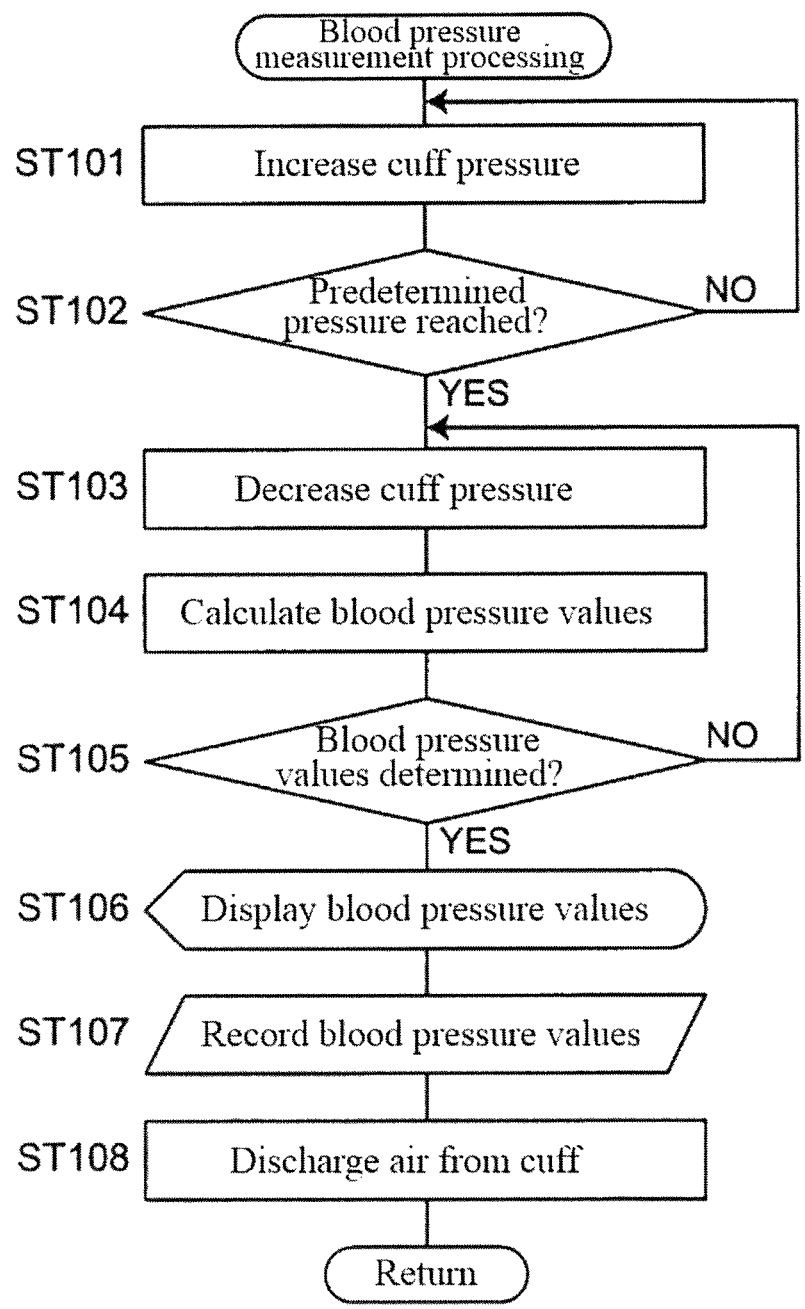
FIG. 9 is a flowchart illustrating blood pressure measurement processing executed by the blood pressure meter 1 shown in FIG. 1.

FIG. 9 is a flowchart of blood pressure measurement processing executed by the blood pressure meter 1 shown in FIG. 1. In general, the following operations are performed when blood pressure measurement is performed according to an ordinary oscillometric method. To be specific, the cuff is wrapped around the measurement area (wrist or the like) of the user in advance, and during measurement, the pump and the valve are controlled to increase the cuff pressure to be higher than the highest blood pressure and thereafter gradually decrease the cuff pressure. In the pressure decrease process, the cuff pressure is detected by the pressure sensor, and a variation in arterial volume that occurs in the arteries running through the measurement area is taken as a pulse wave signal. The highest blood pressure (systolic blood pressure) and the lowest blood pressure (diastolic blood pressure) are calculated based on changes (mainly a leading edge and a trailing edge) in amplitude of the pulse wave signal due to changes in the cuff pressure at that time.

In the blood pressure meter 1, the blood pressure values of the user are measured according to an oscillometric method by the CPU 100 in accordance with the flowchart shown in FIG. 9.

To be specific, in response to the blood pressure measurement switch 52B being pressed while the power supply switch 52A is on, as shown in FIG. 9, the blood pressure meter 1 starts blood pressure measurement. Upon starting a blood pressure measurement, the CPU 100 initializes a processing memory area and outputs a control signal to the valve driving circuit 180. The valve driving circuit 180 opens the valve 18 based on the control signal so as to discharge the air in the fluid bladder 22 of the belt 20. Next, control for adjusting the pressure sensor 16 to 0 mmHg is performed.

In FIG. 9, when blood pressure measurement starts, first, the CPU 100 closes the valve 18 via the valve driving circuit 180, and after that, drives the piezoelectric pump 17 via the pump driving circuit 170 so as to perform processing to increase pressure to send air to the fluid bladder 22. Accordingly, the fluid bladder 22 is inflated and the cuff pressure is gradually increased (step ST101).

When the cuff pressure has increased and reaches a predetermined pressure (YES in step ST102), the CPU 100 performs control for stopping the piezoelectric pump 17 via the pump driving circuit 170 and thereafter gradually opening the valve 18 via the valve driving circuit 180. Accordingly, the fluid bladder 22 contracts and the cuff pressure gradually decreases (step ST103).

As used herein, the predetermined pressure refers to a pressure value that is sufficiently higher than the systolic blood pressure (for example, a systolic blood pressure of +30 mmHg) of the user, and the predetermined pressure is stored in the memory 51 in advance or the CPU 100 determines the predetermined pressure by estimating the systolic blood pressure using a predetermined calculation method while the cuff pressure is increased (see, for example, JP 2001-70263A).

Also, for the pressure decrease speed, a target pressure decrease speed that is a target is set while the cuff pressure is increased, and the CPU 100 controls the opening degree of the valve 18 so as to reach the target pressure decrease speed (see JP 2001-70263A).

In the pressure decrease process, the pressure sensor 16 detects a cuff pressure signal (indicated by a reference sign Pc) representing the pressure of the belt 20 via the belt 20. Based on the cuff pressure signal Pc, the CPU 100 calculates the blood pressure values (systolic blood pressure and diastolic blood pressure) by applying an algorithm, which will be described later, using an oscillometric method (step ST104). Note that the calculation of the blood pressure values is not limited to being performed in the pressure decrease process, and may be performed in the pressure increase process.

Upon determining the blood pressure values through calculation (YES in step ST105), the CPU 100 performs control for displaying the calculated blood pressure values on the display device 50 (step ST106) and also performs control for storing the calculated blood pressure values in the memory 51 (step ST107).

Next, the CPU 100 performs control for opening the valve 18 via the valve driving circuit 180 so as to discharge the air in the fluid bladder 22 of the belt 20 (step ST108).

After that, in response to the power supply switch 52A being pressed, the blood pressure measurement ends.

When detaching the blood pressure meter 1 from the wrist 90, the user opens the first plate frame member 30a and the second plate frame member 30b of the buckle 30, and releases the wrist 90 from the belt with the loop of the belt 20 being widened.

When wearing the blood pressure meter 1 on the wrist 90 for the second time or more, the user can insert the wrist 90 through the loop of the belt 20, with the first plate frame member 30a and the second plate frame member 30b of the buckle 30 being open, and close the buckle 30. Accordingly, the user can easily wear the blood pressure meter 1 on the wrist 90.

Figure 10A:
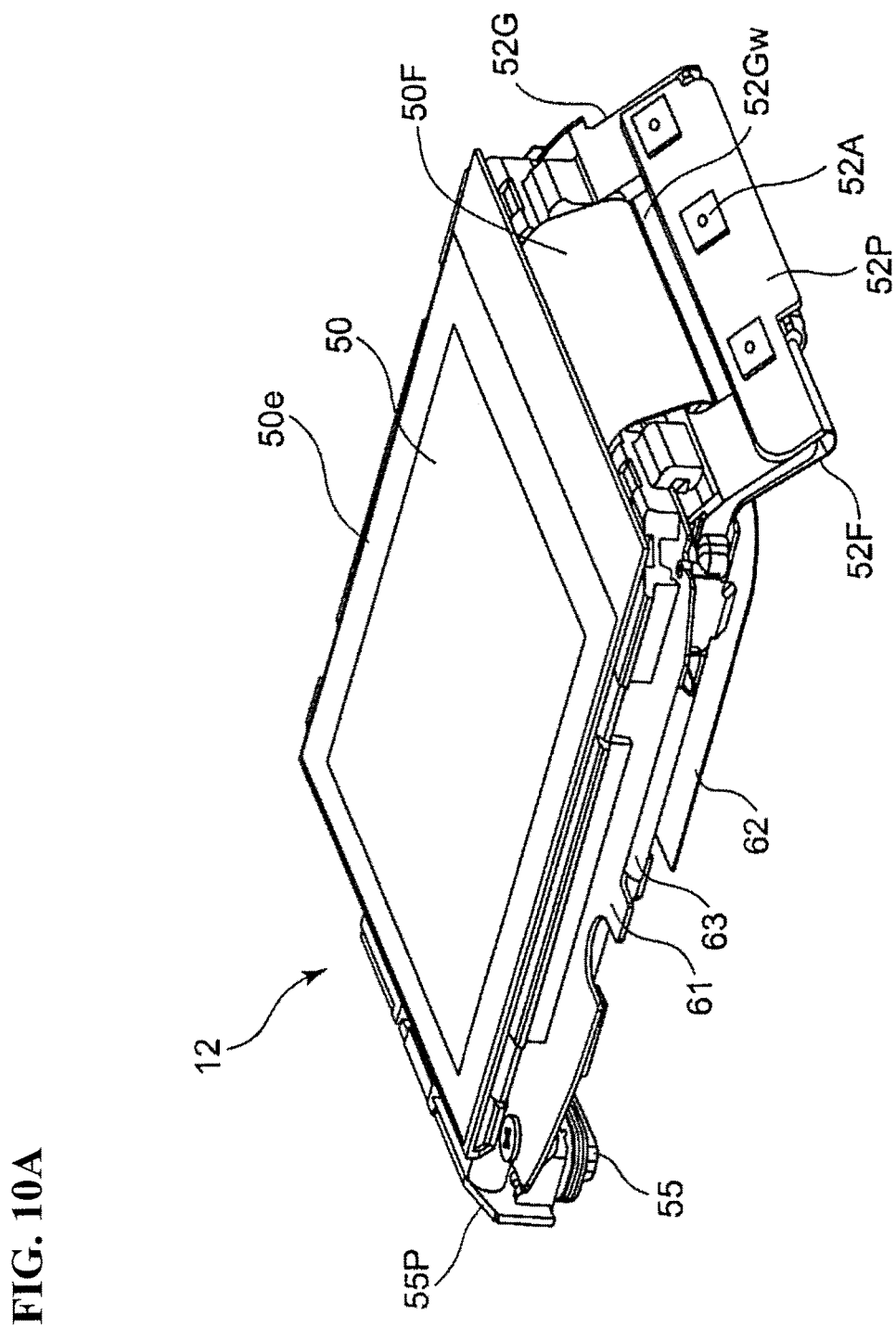
FIG. 10A is an enlarged view of a main body assembly 12 shown in FIG. 5.
Figure 10B:
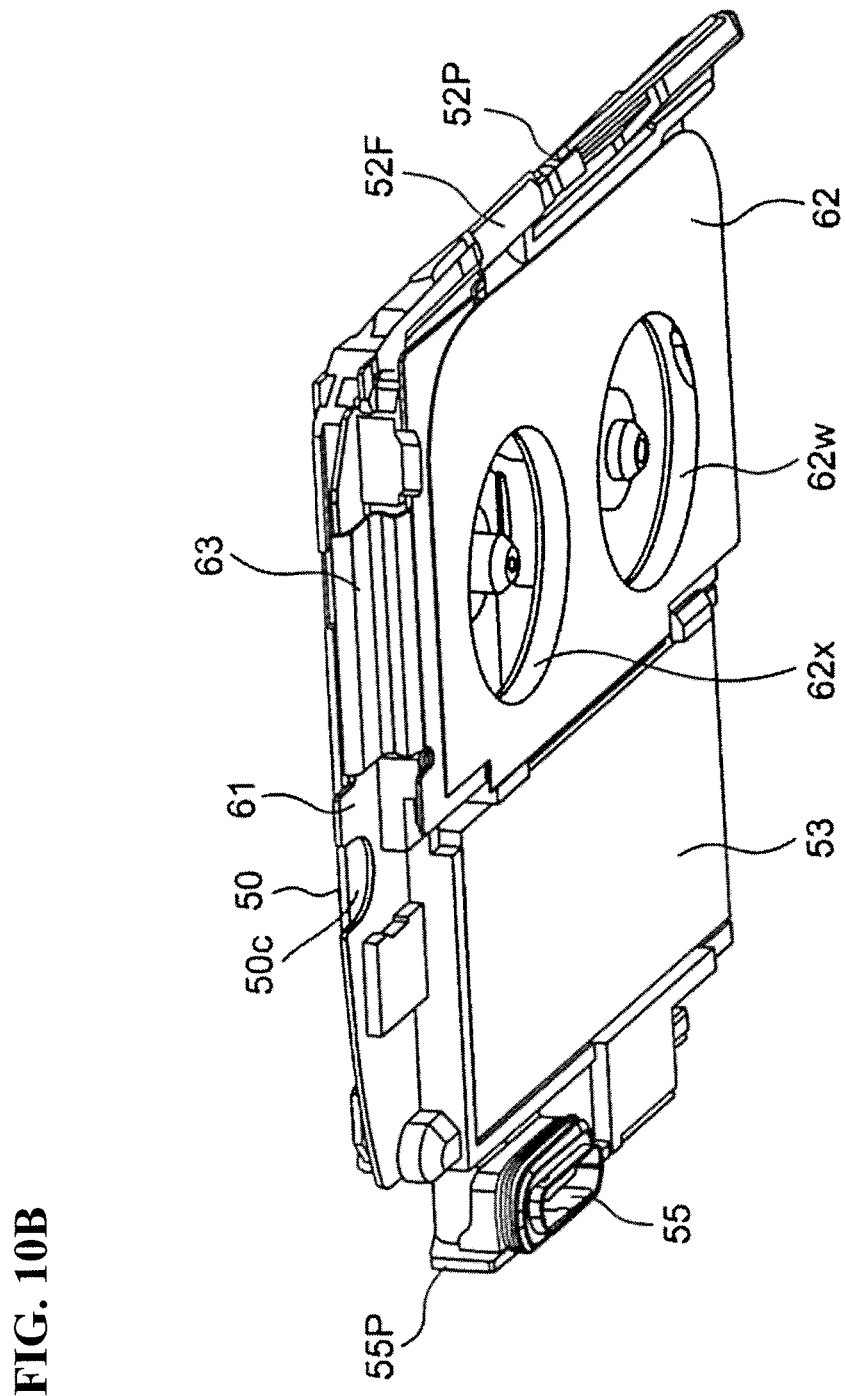
FIG. 10B is a bottom view of the main body assembly 12 as viewed from the bottom in FIG. 10A.
Figure 11:
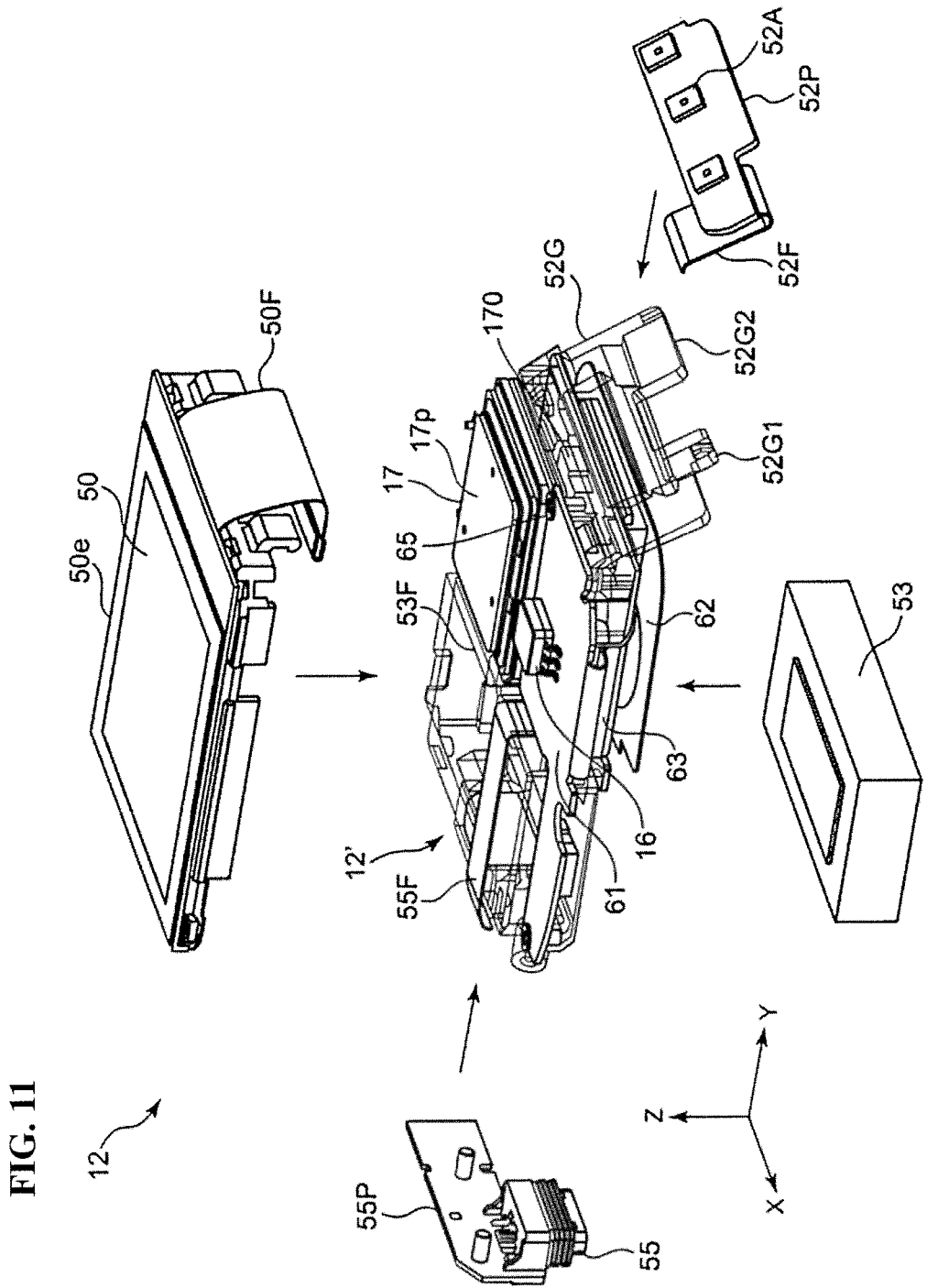
FIG. 11 is an exploded view of the main body assembly 12 shown in FIG. 10A.

FIG. 10A is an enlarged view of the main body assembly 12 shown in FIG. 5. FIG. 10B is a bottom view of the main body assembly 12 as viewed from the bottom in FIG. 10A. FIG. 11 is an exploded view of the main body assembly 12 shown in FIG. 10A. In FIG. 11, an XYZ orthogonal coordinate system is also shown where a direction (the thickness direction of the main body assembly 12) that is vertical to the outer circumferential surface of the wrist 90 that serves as the measurement area is defined as a Z direction, a direction corresponding to the width direction of the belt 20 is defined as an X direction, and a direction corresponding to the lengthwise direction of the belt 20 is defined as a Y direction (the same applies to FIGS. 12 to 15, 16(B), 17, and 18, which will be described later).

As can be clearly seen from FIG. 11, the main body assembly 12 includes a sub-assembly 12' that includes, at a substantially center position, an upper substrate 61 that serves as a first substrate and a lower substrate 62 that serves as a second substrate that opposes the upper substrate 61 and is combined with the upper substrate 61 in the Z direction. The upper substrate 61 is attached to the lower substrate 62 with a screw 65 or the like via a spacer (not shown in the diagram) so as to provide a fixed spacing with respect to the lower substrate 62 in the Z direction. As used herein, the terms "upper substrate" and "lower substrate" (as well as the terms "upper surface" and "lower surface" which will be described later) are used for the sake of the description, and thus are not intended to limit the orientation of the blood pressure meter 1 when in use.

On the upper substrate 61, the pressure sensor 16, the CPU 100 (including the oscillation circuit 160) and the memory 51 that were described above and an interconnect are mounted (for the sake of simplification, only the pressure sensor 16 is shown in FIG. 11). On the lower substrate 62, the piezoelectric pump 17, the pump driving circuit 170, the valve 18 and the valve driving circuit 180 that were described above and an interconnect are mounted (for the sake of simplification, only the piezoelectric pump 17 and the pump driving circuit 170 are shown in FIG. 11). The interconnect of the upper substrate 61 and the interconnect of the lower substrate 62 are connected to each other by the FPC cable 63.

The upper substrate 61 has a dimension in the X direction that is substantially half of the dimension in the X direction of the lower substrate 62. With this configuration, the upper substrate 61 opposes only substantially half of the region of the lower substrate 62 that is on the +X side in the X direction. The piezoelectric pump 17 includes a main portion 17p having a rectangular parallelepipedal shaped outer contour, and is mounted on substantially half of the region of the lower substrate 62 that is on the −X side in the X direction. The piezoelectric pump 17 is higher than the upper substrate 61, as a result of which, the piezoelectric pump 17 is located at a position adjacent to the upper substrate 61 on the −X side in a planar direction (XY direction).

Substantially half of the region of the sub-assembly 12' that is on the −Y side in the Y direction is occupied by a frame-shaped battery holder 53F. The battery 53 having a rectangular parallelepipedal shaped outer contour is fitted and attached to the battery holder 53F from the −Z direction. As a result, the upper substrate 61, the piezoelectric pump 17, the lower substrate 62, and the attached battery 53 form a rectangular parallelepipedal shaped outer contour as a whole. As a result of these elements being assembled in a compact design, it is possible to promote miniaturization of the product.

The main body assembly 12 further includes a USB substrate 55P attached to an edge portion of the upper substrate 61 that is on the −Y side. The USB substrate 55P incorporates a USB terminal 55 and an interconnect (not shown). The interconnect of the USB substrate 55P is connected to the interconnect of the upper substrate 61 via an FPC cable 55F.

Also, the main body assembly 12 includes a plate-like joint member 52G that is attached to an edge portion of the lower substrate 62 that is on the +Y side, and is inclined in the −Z direction. The joint member 52G includes two branched tip ends 52G1 and 52G2. A switch substrate 52P incorporating the power supply switch 52A and an interconnect (not shown) is attached so as to straddle the tip ends 52G1 and 52G2. The interconnect of the switch substrate 52P is connected to the interconnect of the lower substrate 62 via an FPC cable 52F.

Also, the main body assembly 12 includes the substantially flat plate-like display device 50 (an organic EL (electro luminescent) display in this example) that is attached to the outside (on +Z side). The display device 50 includes a rectangular frame-shaped glass frame 50e extending along a peripheral edge of the display device 50, and also includes a metal plate 50c on a back surface of the display device 50. Also, an FPC cable 50F is attached to an edge portion of the display device 50 that is on the +Y side. The FPC cable 50F passes through a gap 52Gw (see FIG. 10A) formed between the joint member 52G and the switch substrate 52P, and is connected to the interconnect of the lower substrate 62.

As described above, the main body assembly 12 shown in FIGS. 10A and 10B is configured in a compact and substantially rectangular parallelepipedal shape.

Figure 12:
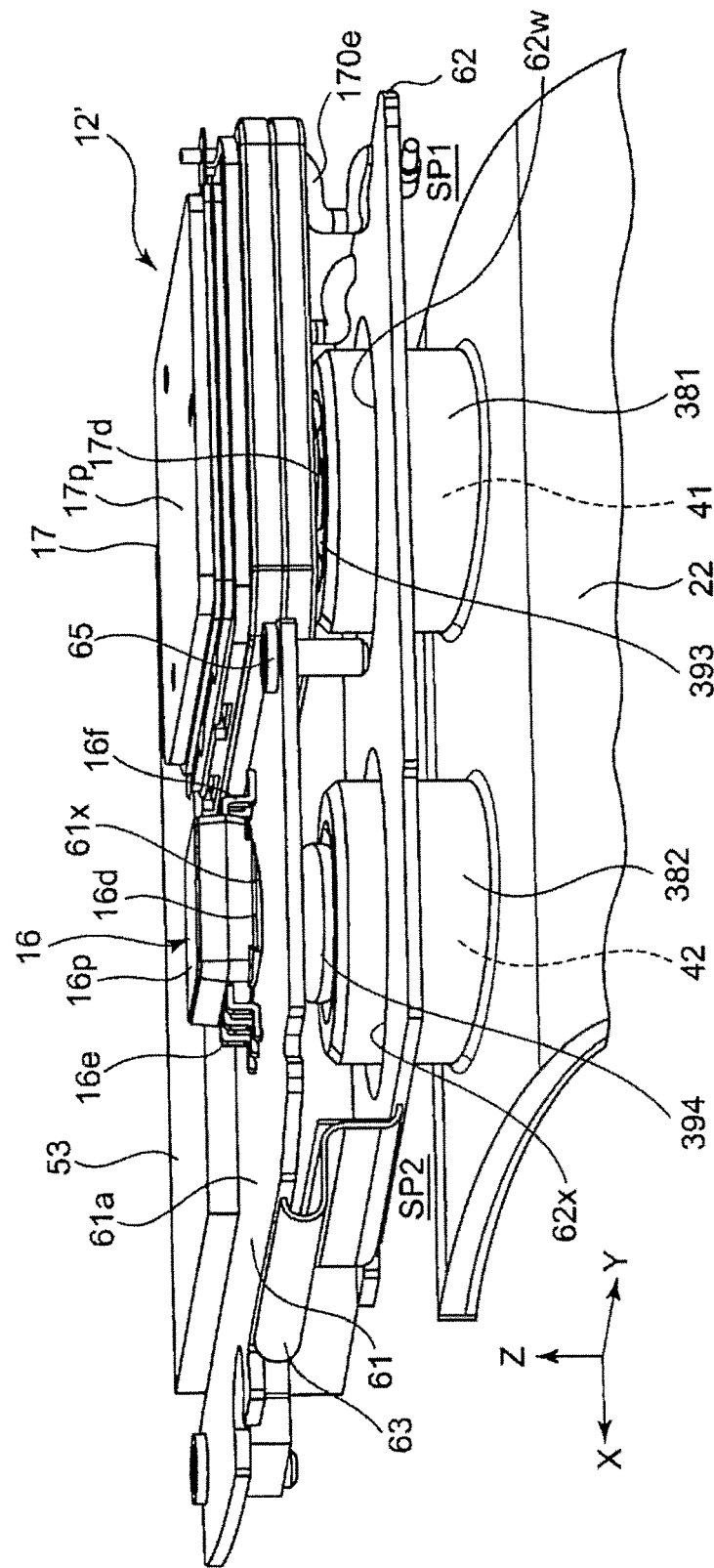
FIG. 12 is a perspective view showing a positional relationship between a sub-assembly 12' and a fluid bladder 22 in the assembled blood pressure meter 1.
Figure 13:
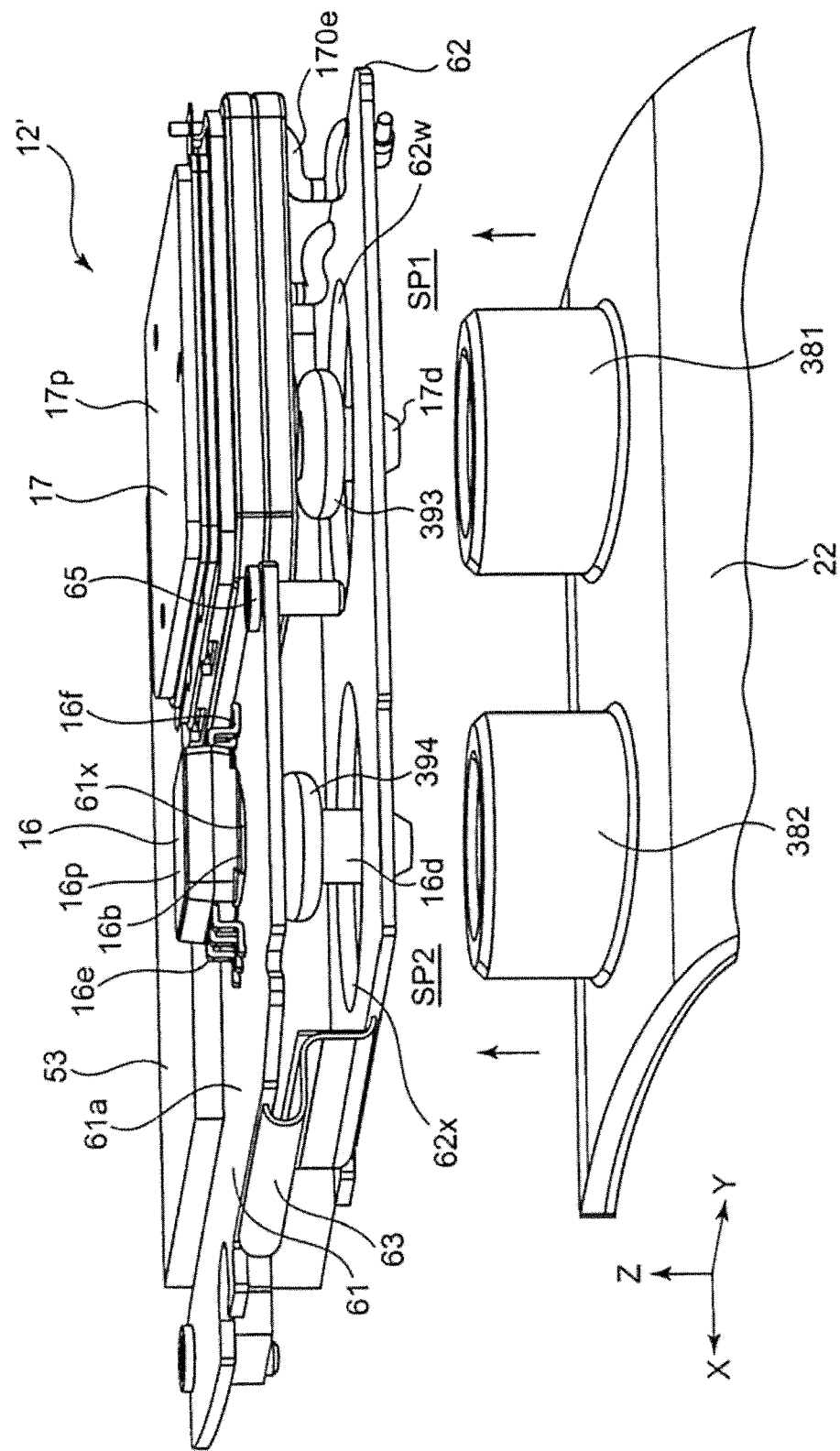
FIG. 13 is a diagram showing a state in which the sub-assembly 12' and the fluid bladder 22 shown in FIG. 12 are spaced apart in a thickness direction (Z direction).

FIG. 12 shows a positional relationship between the sub-assembly 12' and the fluid bladder 22 in the assembled blood pressure meter 1, as viewed obliquely. FIG. 13 shows a state (state before assembly) in which the sub-assembly 12' and the fluid bladder 22 shown in FIG. 12 are spaced apart in the Z direction. For the sake of ease of understanding, in FIGS. 12 and 13, the illustration of the lower housing 13 is omitted. The fluid bladder 22 includes cylindrical nipples 381 and 382 for allowing air to be supplied into the fluid bladder 22 as a fluid and allowing air to be discharged from the fluid bladder 22.

As can be clearly seen from FIG. 13, the pressure sensor 16 is incorporated in a substantially rectangular parallelepipedal shape sensor package 16p and mounted on the upper surface 61a of the upper substrate 61. In this example, the pressure sensor 16 includes a substantially cylindrical inlet pipe 16d that is integrally molded with the sensor package 16p and lead terminals 16e and 16f that protrude from side surfaces of the sensor package 16p. The lead terminals 16e and 16f are connected to the interconnect (not shown) that is provided on the upper substrate 61. The inlet pipe 16d extends straight in the −Z direction from a bottom surface (a surface that is closer to the upper substrate 61) 16b of the sensor package 16p toward the fluid bladder 22 through a through hole 61x that is formed in the upper substrate 61 and a through hole 62x that is formed in the lower substrate 62 and serves as an escaping portion. The inlet pipe 16d constitutes a portion of a circumferential wall of the second fluid path 42 described above. An O ring 394 for hermetic sealing is press fitted around the inlet pipe 16d. The sensor package 16p and the inlet pipe 16d may be formed separately, and integrally jointed with an adhesive or the like.

The piezoelectric pump 17 is mounted on the lower substrate 62, and, as already described above, is located at a position adjacent to the upper substrate 61 on the −X side in the planar direction (the XY direction). The piezoelectric pump 17 includes the main portion 17p having a rectangular parallelepipedal shaped outer contour and a substantially cylindrical outlet pipe 17d integrally molded with the main portion 17p. The outlet pipe 17d extends straight in the −Z direction from a bottom surface of the main portion 17p toward the fluid bladder 22 through a through hole 62w that is formed in the lower substrate 62 and that serves as another escaping portion. The outlet pipe 17d constitutes a portion of a circumferential wall of the first fluid path 41 described above. An O ring 393 for hermetic sealing is press fitted around the outlet pipe 17d.

As can be clearly seen from FIG. 12, in the assembled blood pressure meter 1, the nipples 381 and 382 of the fluid bladder 22 are provided around the outlet pipe 17d of the piezoelectric pump 17 and the inlet pipe 16d of the pressure sensor 16 so as to overlap them in the Z direction through the through holes 62w and 62x formed in the lower substrate 62, thereby constituting the first fluid path 41 and the second fluid path 42, respectively. The through holes 62w and 62x that are formed in the lower substrate 62 and serve as escaping portions are configured to have an inner diameter slightly larger than the outer diameter of outer circumferential cylindrical portions 391a and 392a of the lower housing 13, which will be described later.

Figure 14:
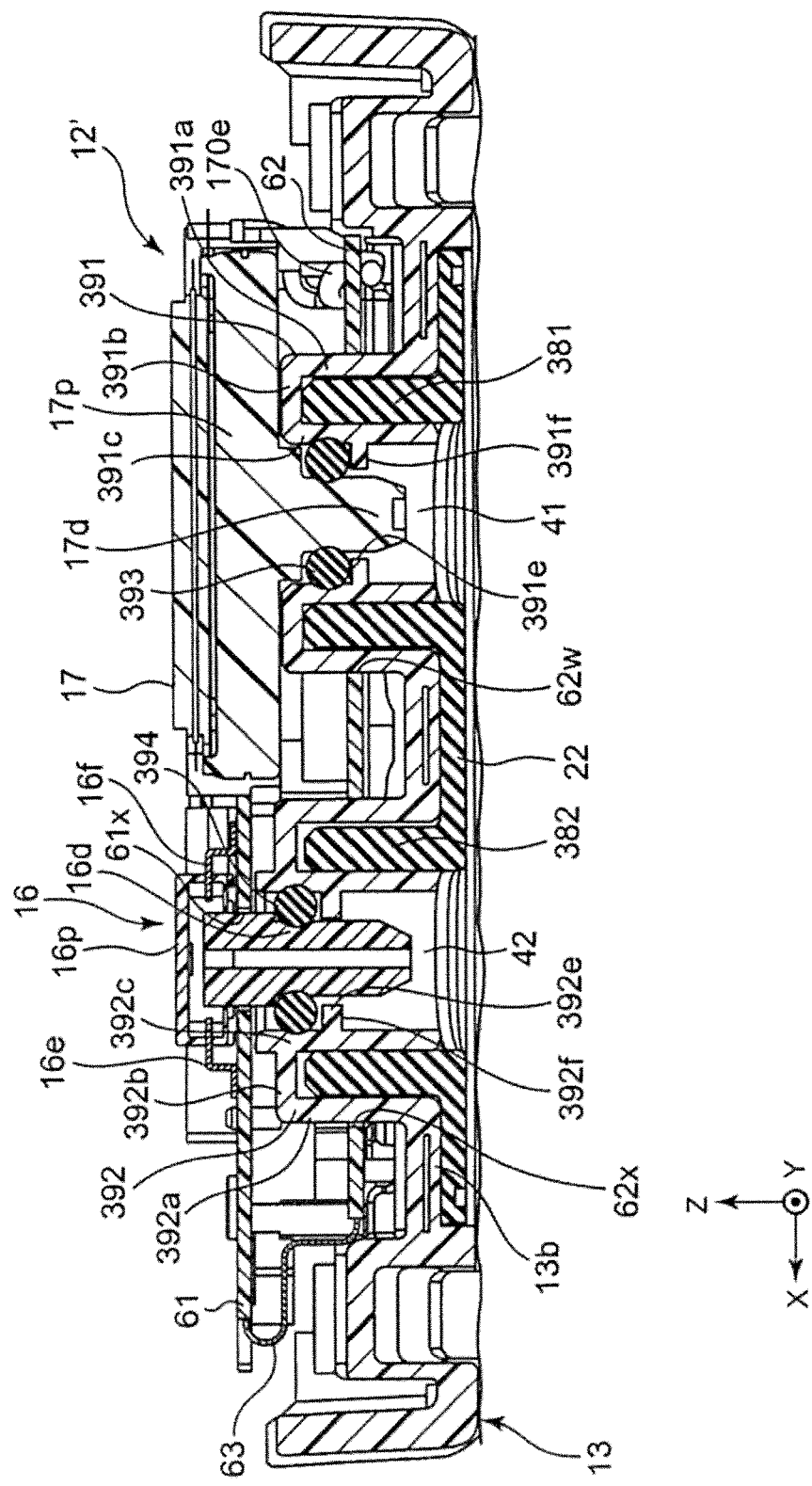
FIG. 14 is a ZX cross-sectional view through a pressure sensor 16, showing, in detail, a configuration of a first fluid path 41 and a second fluid path 42 in the blood pressure meter 1, together with a lower housing 13 provided between the sub-assembly 12' and the fluid bladder 22.
Figure 15:
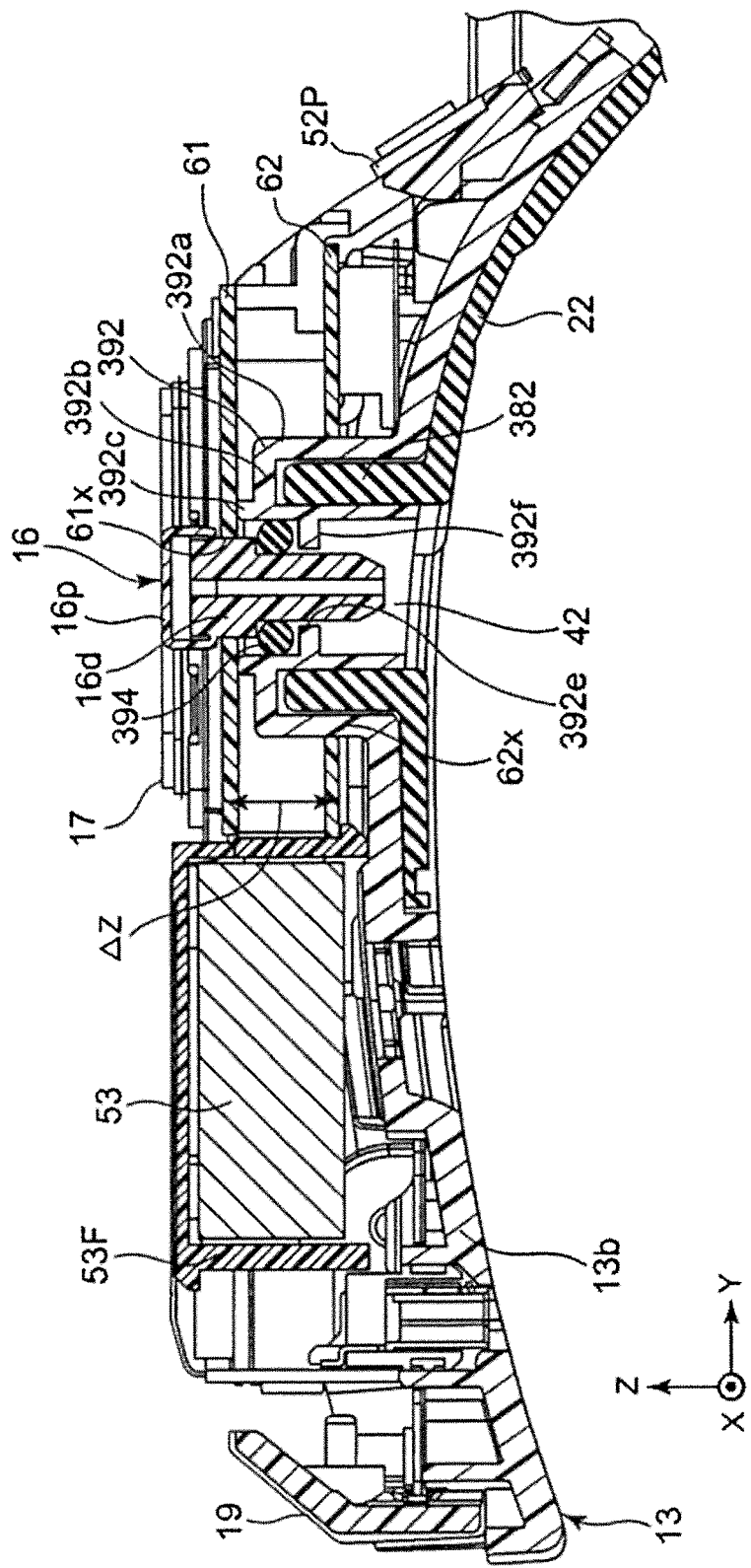
FIG. 15 is a YZ cross-sectional view through the pressure sensor 16, showing, in detail, a configuration of the second fluid path 42 in the blood pressure meter 1, together with the lower housing 13 provided between the sub-assembly 12' and the fluid bladder 22, so as to realize hermetic sealing.

FIG. 14 shows, in detail, a configuration of the first fluid path 41 and the second fluid path 42, together with the lower housing 13 provided between the sub-assembly 12' and the fluid bladder 22, by using a ZX cross-sectional view through the pressure sensor 16. Also, FIG. 15 shows, in detail, a configuration of the second fluid path 42, together with the lower housing 13 provided between the sub-assembly 12' and the fluid bladder 22, by using a YZ cross-sectional view through the pressure sensor 16.

As can be clearly seen from FIG. 14, the lower housing 13 includes double cylindrical portions 391 and 392 at positions corresponding to the outlet pipe 17d of the piezoelectric pump 17 and the inlet pipe 16d of the pressure sensor 16, respectively, on a bottom wall 13b of the lower housing 13.

The double cylindrical portion 391 includes an outer circumferential cylindrical portion 391a that stands upright from the bottom wall 13b in the +Z direction, an inner circumferential cylindrical portion 391c that is concentric with the outer circumferential cylindrical portion 391a, and extends in the Z direction through the bottom wall 13b, and an annular joint plate portion 391b that is flat and joins an upper edge of the outer circumferential cylindrical portion 391a and an upper edge of the inner circumferential cylindrical portion 391c to each other. On the inner circumferential side of the inner circumferential cylindrical portion 391c, an annular engaging plate portion 391f is provided in a protruding manner at a substantially center position in the Z direction so as to reduce the diameter (inner diameter). The engaging plate portion 391f has an inner circumferential edge 391e configured to have a diameter (inner diameter) slightly larger than the outer diameter of the outlet pipe 17d of the piezoelectric pump 17. Also, the inner circumferential cylindrical portion 391c is configured to have an inner diameter slightly smaller than the outer diameter of the O ring 393. The inner circumferential cylindrical portion 391c is configured to have an outer diameter slightly larger than the inner diameter of the nipple 381. A radial spacing between the inner circumferential cylindrical portion 391c and the outer circumferential cylindrical portion 391a is configured to be sufficiently larger than the thickness of the nipple 381 of the fluid bladder 22 so as to allow insertion of the nipple 381 of the fluid bladder 22 into the spacing.

Likewise, the double cylindrical portion 392 includes an outer circumferential cylindrical portion 392a that stands upright from the bottom wall 13b in the +Z direction, an inner circumferential cylindrical portion 392c that is concentric with the outer circumferential cylindrical portion 392a, and extends in the Z direction through the bottom wall 13b, and an annular joint plate portion 392b that is flat and joins an upper edge of the outer circumferential cylindrical portion 392a and an upper edge of the inner circumferential cylindrical portion 392c to each other. On the inner circumferential side of the inner circumferential cylindrical portion 392c, an annular engaging plate portion 392f is provided in a protruding manner at a substantially center position in the Z direction so as to reduce the diameter (inner diameter). The engaging plate portion 392f has an inner circumferential edge 392e configured to have a diameter (inner diameter) slightly larger than the outer diameter of the inlet pipe 16d of the pressure sensor 16. Also, the inner circumferential cylindrical portion 392c is configured to have an inner diameter slightly smaller than the outer diameter of the O ring 394. The inner circumferential cylindrical portion 392c is configured to have an outer diameter slightly larger than the inner diameter of the nipple 382. A radial spacing between the inner circumferential cylindrical portion 392c and the outer circumferential cylindrical portion 392a is configured to be sufficiently larger than the thickness of the nipple 382 of the fluid bladder 22 so as to allow insertion of the nipple 382 of the fluid bladder 22 into the spacing.

With this configuration, in a state in which the blood pressure meter 1 is assembled and the sub-assembly 12' (the main body assembly 12) is attached to the lower housing 13, the outlet pipe 17d of the piezoelectric pump 17 extends in the −Z direction beyond the inner circumferential edge 391e of the engaging plate portion 391f of the inner circumferential cylindrical portion 391c. At the same time, the O ring 393 is press fitted into the inner circumferential cylindrical portion 391c so as to realize hermetic sealing between the outlet pipe 17d and the inner circumferential cylindrical portion 391c. Likewise, the inlet pipe 16d of the pressure sensor 16 extends in the −Z direction beyond the inner circumferential edge 392e of the engaging plate portion 392f of the inner circumferential cylindrical portion 392c. At the same time, the O ring 394 is press fitted into the inner circumferential cylindrical portion 392c so as to realize hermetic sealing between the inlet pipe 16d and the inner circumferential cylindrical portion 392c Furthermore, in a state in which the fluid bladder 22 is attached to the lower housing 13, the nipple 381 of the fluid bladder 22 is press fitted to an outer circumference of the inner circumferential cylindrical portion 391c so as to realize hermetic sealing between the inner circumferential cylindrical portion 391c and the nipple 381. Likewise, the nipple 382 of the fluid bladder 22 is press fitted to an outer circumference of the inner circumferential cylindrical portion 392c so as to realize hermetic sealing between the inner circumferential cylindrical portion 392c and the nipple 382.

With this configuration, in the assembled blood pressure meter 1, the outlet pipe 17d of the piezoelectric pump 17 and the nipple 381 of the fluid bladder 22 are hermetically attached to the inner circumferential cylindrical portion 391c of the bottom wall 13b of the lower housing 13, as a result of which, the first fluid path 41 extending straight in the Z direction is formed between the piezoelectric pump 17 and the fluid bladder 22. Likewise, the inlet pipe 16d of the pressure sensor 16 and the nipple 382 of the fluid bladder 22 are hermetically attached to the inner circumferential cylindrical portion 392c, as a result of which, the second fluid path 42 extending straight in the Z direction is formed between the pressure sensor 16 and the fluid bladder 22.

Here, if a configuration is applied in which the inlet pipe 16d of the pressure sensor 16 and the nipple 382 of the fluid bladder 22 can be directly fitted and attached, stress may be applied to the pressure sensor 16 from the nipple 382 via the inlet pipe 16d and the sensor package 16p during assembly, which may compromise the characteristics of the pressure sensor 16. However, with the blood pressure meter 1, the inlet pipe 16d of the pressure sensor 16 and the nipple 382 that is in communication with the fluid bladder 22 are hermetically attached to the inner circumferential cylindrical portion 392c of the bottom wall 13b. Accordingly, it is possible to independently perform an operation to attach the inlet pipe 16d of the pressure sensor 16 to the inner circumferential cylindrical portion 392c of the bottom wall 13b and an operation to attach the nipple 382 that is in communication with the fluid bladder 22 to the inner circumferential cylindrical portion 392c of the bottom wall 13b. Thus, there is no possibility that the characteristics of the pressure sensor 16 will be compromised due to the application of stress from the nipple 382 during assembly. As a result, the reliability of assembly is enhanced.

Also, as described above, the through holes 62w and 62x that are formed in the lower substrate 62 and serve as escaping portions are configured to have an inner diameter slightly larger than the outer diameter of the outer circumferential cylindrical portions 391a and 392a, which will be described later. Accordingly, the lower substrate 62 does not interfere with the first fluid path 41 and the second fluid path 42.

Also, in this example, the lower substrate 62 on which the blood pressure measurement elements 170, 18, 180, . . . are mounted in addition to the piezoelectric pump 17 is disposed in spaces SP1 and SP2 (see FIG. 12) that are located between the upper substrate 61 and the fluid bladder 22 in the Z direction and around the first fluid path 41 and the second fluid path 42 in the XY direction. Accordingly, the spaces SP1 and SP2 can be effectively used by the lower substrate 62. As a result, it is possible to promote miniaturization of the product, in particular, miniaturization in the planar direction (the XY direction).

To be specific, if a configuration is applied in which the blood pressure measurement elements 17, 170, 18, 180, . . . that need to be mounted on the lower substrate 62 are mounted on the upper substrate 61 in the absence of the lower substrate 62, there is no option but to increase the dimension in the XY direction of the upper substrate 61 accordingly (by an amount corresponding to the increased region where the blood pressure measurement elements are disposed). However, with the blood pressure meter 1, the spaces SP1 and SP2 where a component is not disposed in a conventional blood pressure meter can be effectively used by the lower substrate 62. As a result, the dimension in the XY direction of the upper substrate 61 can be reduced, and miniaturization in the XY direction can be promoted.

Also, as can be clearly seen from FIG. 15, in this example, the battery 53 continuously occupies a range ΔZ in which at least the upper substrate 61 and the lower substrate 62 are disposed in the Z direction. As a result, the capacity of the battery 53 can be increased.

FIGS. 16(A) and 16(B) show, in a laid-out state, the upper substrate 61 and the lower substrate 62 that are connected to each other by the FPC cable 63 before the sub-assembly 12' is assembled. FIG. 16(A) shows the upper surface 61a of the upper substrate 61 and the lower surface 62b of the lower substrate 62. FIG. 16(B) shows the lower surface 61b of the upper substrate 61 and the upper surface 62a of the lower substrate 62, which corresponds to the back side of FIG. 16(A). In the sub-assembly 12' (the main body assembly 12), the upper substrate 61 is disposed above the lower substrate 62 so as to oppose the lower substrate 62 as a result of the FPC cable 63 being bent as indicated by the arrow F in FIG. 16(B). In FIGS. 16(A) and 16(B), the USB substrate 55P connected to the upper substrate 61 by the FPC cable 55F and the switch substrate 52P connected to the lower substrate 62 by the FPC cable 52F are also shown.

As can be clearly seen from FIG. 16(A), in the upper substrate 61, a region 61$u$ in which the pressure sensor 16 is mounted is provided adjacent to a region 61$v$ in which the CPU 100 (including the oscillation circuit 160) is mounted. Accordingly, the interconnect between the pressure sensor 16 and the CPU 100 is relatively short, which makes it unlikely that noise will be included in the output of the pressure sensor 16. As a result, the accuracy of blood pressure measurement is enhanced. The upper substrate 61 includes a substantially rectangular island shaped portion 61$s$ that protrudes in an upper right diagonal direction in FIG. 16(A). The island shaped portion 61$s$ includes a contact electrode 53$s$ that is connected to the battery 53.

Also, as can be clearly seen from FIG. 16(B), a region 62$u$ of the substantially rectangular lower substrate 62 in which the pump driving circuit 170 is mounted is provided to be spaced apart from the region 61$u$ of the upper substrate 61 in which the pressure sensor 16 is mounted in the planar direction (the XY direction) (rather, the region 61$u$ opposes the piezoelectric pump 17 shown in FIG. 12). Furthermore, in order to transmit a drive current from the pump driving circuit 170 to the piezoelectric pump 17, a lead wire 170$e$ (see FIG. 12) that electrically connects the lower substrate 62 and the piezoelectric pump 17 is connected to an end portion of the piezoelectric pump 17 that is on the opposite side of the pressure sensor 16 in the planar direction (the XY direction). Accordingly, the distance from the pressure sensor 16 to the pump driving circuit 170 and the lead wire 170$e$ is increased, and thus heat generated in the pump driving circuit 170 and the lead wire 170$e$ due to the electric current that drives the piezoelectric pump 17 is unlikely to be transferred to the pressure sensor 16. As a result, the output of the pressure sensor 16 is unlikely to be affected by the generated heat, and the accuracy of blood pressure measurement is further enhanced.

Also, as can be seen from FIGS. 11 and 10A, in the assembled main body assembly 12, at least the region 61$u$ of the upper substrate 61 in which the pressure sensor 16 is mounted and the region 61$v$ of the upper substrate 61 in which the CPU 100 is mounted shown in FIG. 16(A) are shielded, in the thickness direction (Z direction), by the display device 50 including the metal plate 50$c$ that is disposed extending outward of the upper substrate 61 and the lower substrate 62 that is disposed extending inward of the upper substrate 61. Accordingly, this makes it more unlikely that noise will be included in the output of the pressure sensor 16. As a result, the accuracy of blood pressure measurement is further enhanced.

Figure 17:
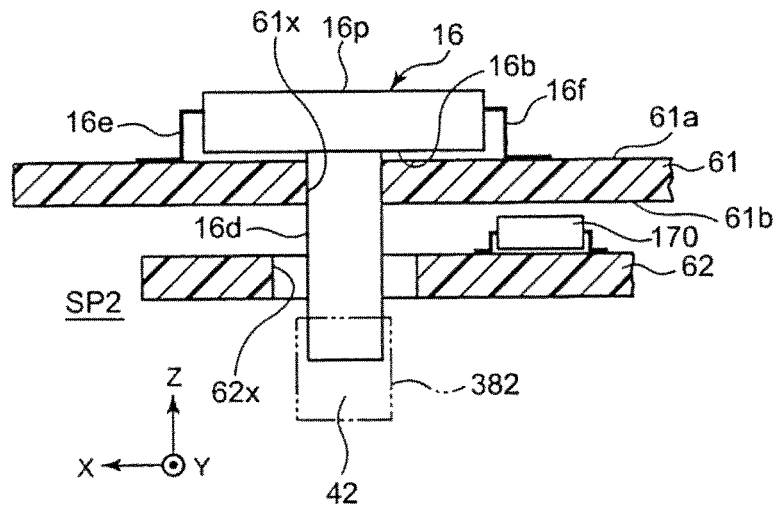
FIG. 17 is a schematic diagram showing a configuration near the pressure sensor 16 mounted on the upper surface 61a of the upper substrate 61.
Figure 18:
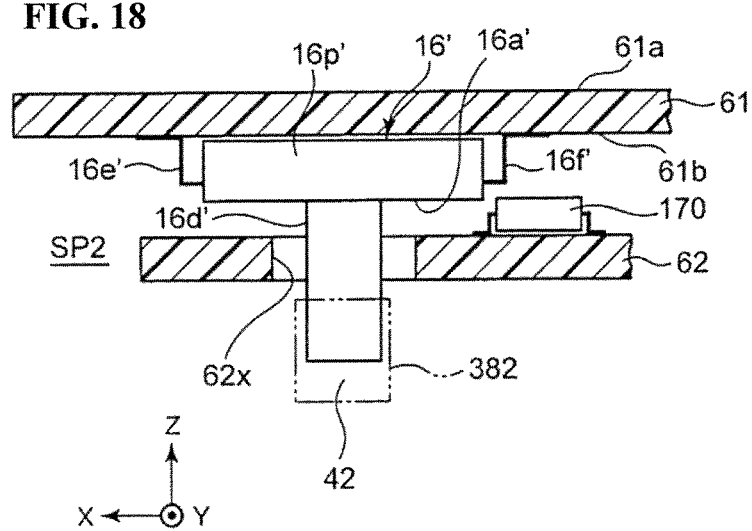
FIG. 18 is a schematic diagram showing a configuration near a pressure sensor 16' mounted on a lower surface 61b of the upper substrate 61.

The embodiment described above is configured such that, as schematically shown in FIG. 17, the pressure sensor 16 is incorporated in the substantially rectangular parallelepipedal shape sensor package 16$p$ and mounted on the upper surface 61$a$ of the upper substrate 61. However, the configuration is not limited thereto. For example, as shown in FIG. 18, a pressure sensor 16' may be incorporated in a substantially rectangular parallelepipedal sensor package 16$p$' and mounted on the lower surface 61$b$ of the upper substrate 61. In this case, lead terminals 16$e$' and 16$f$' of the pressure sensor 16' are connected to an interconnect (not shown) provided on the lower surface 61$b$ of the upper substrate 61. An inlet pipe 16$d$' extends straight in the −Z direction from a surface 16$a$' of the sensor package 16$p$' that is distant from the upper substrate 61 toward the fluid bladder 22 through the through hole 62$x$ that is formed in the lower substrate 62 and serves as an escaping portion. In the example shown in FIG. 18 as well, a space SP2 around the second fluid path 42 (and a space SP1 around the first fluid path 41) where a component is not disposed in a conventional blood pressure meter can be effectively used by the lower substrate 62. As a result, the dimension in the XY direction of the upper substrate 61 can be reduced, and miniaturization in the XY direction can be promoted.

Also, the embodiment described above is configured such that, as shown in, for example, FIGS. 12 and 13, the through holes 62$w$ and 62$x$ that are formed in the plane surface of the lower substrate 62, or in other words, that are formed internally in the planar direction (the XY direction) are used as the escaping portions formed in the lower substrate 62. However, the configuration is not limited thereto. The escaping portions formed in the lower substrate 62 may be cut-out portions formed in the peripheral edge of the lower substrate 62.

Also, the embodiment described above is configured such that the main body 10 of the blood pressure meter 1 is disposed in the base end portion $a$ in the lengthwise direction of the belt 20, but the configuration is not limited thereto. The main body 10 may be disposed in, for example, a center portion in the lengthwise direction of the belt 20.

The above-described embodiment is merely an example, and various modifications are possible without departing from the scope of the present invention. Also, multiple embodiments described above can be achieved independently or in combination with each other. Also, various characteristics of different embodiments can be achieved independently or in combination with each other.

REFERENCE NUMERALS LIST

1 Blood pressure meter
10 Main body
16 Pressure sensor
17 Piezoelectric pump
18 Valve
20 Belt
22 Fluid bladder
23 Reinforcing layer
24 Outer circumferential layer
25 Engaged portion
29 Sheet
30 Buckle
30$a$ First plate frame member
30$b$ Second plate frame member
31 Projection portion
32 Engaging portion
33 Magnet
41 First fluid path
42 Second fluid path
50 Display device
51 Memory
52 Operation unit
52A Power supply switch
52B Blood pressure measurement switch
53 Battery
61 Upper substrate
62 Lower substrate
61$x$, 62$w$, 62$x$ Through hole
160 Oscillation circuit
170 Pump driving circuit 180 Valve driving circuit
100 CPU

The invention claimed is:

1. A blood pressure meter configured to be wrapped around a measurement area having pulsatile properties, the blood pressure meter comprising:
a strip-shaped belt that includes a fluid bladder to which a fluid is supplied, wherein the belt is configured to be wrapped around the measurement area;
a main body that is provided on an outer surface side of the belt;
a display device disposed on an outside of the main body;
a pump that is provided inside the main body, and is capable of supplying the fluid to the fluid bladder;
a first fluid path that feeds the fluid from the pump to the fluid bladder or discharges the fluid from the fluid bladder;
a pressure sensor that is incorporated in a sensor package and mounted on a first PCB disposed inside the main body, and is capable of detecting the pressure in the fluid bladder; and
a second fluid path that introduces the fluid from the fluid bladder to the pressure sensor,
wherein the second fluid path includes an inlet pipe that is integrally formed with the sensor package as a circumferential wall of the second fluid path, and extends straight between the fluid bladder and the pressure sensor,
wherein a second PCB, on which a blood pressure measurement device is mounted, is disposed in a space that is located between the first PCB and the fluid bladder in a thickness direction and is adjacent to the second fluid path in a planar direction perpendicular to the thickness direction,
wherein the pressure sensor on the first PCB is electrically connected to the blood pressure measurement device on the second PCB, and
wherein the second PCB is disposed within the main body.

2. The blood pressure meter according to claim 1, wherein the second PCB includes an escaping through-hole for allowing the second fluid path to pass therethrough in a plane surface extending along the planar direction.

3. The blood pressure meter according to claim 1,
wherein the pump is disposed at a position adjacent to the first PCB in the planar direction,
wherein the first fluid path includes an outlet pipe of the pump as a circumferential wall of the first fluid path, and extends straight between the pump and the fluid bladder in parallel to the second fluid path, and
wherein the second PCB extends in a space that is located between the pump and the fluid bladder in the thickness direction and is adjacent to the first fluid path in the planar direction.

4. The blood pressure meter according to claim 3, wherein the second PCB includes another escaping through-hole for allowing the first fluid path to pass therethrough in the plane surface extending along the planar direction.

5. The blood pressure meter according to claim 3,
wherein a pump driving circuit for driving the pump is mounted on the second PCB,
wherein a region of the second substrate PCB in which the pump driving circuit is mounted is provided to be spaced apart, in the planar direction, from a region of the first PCB in which the pressure sensor is mounted and to oppose the pump, and
wherein a lead wire that electrically connects the pump driving circuit and the pump is connected to an end portion of the pump, the end portion being on an opposite side of the pressure sensor in the planar direction.

6. The blood pressure meter according to claim 1,
wherein a central processing unit (CPU) that receives an output of the pressure sensor and performs blood pressure calculation processing is mounted on the first PCB, and
wherein a region of the first PCB in which the CPU is mounted is provided adjacent to a region of the first PCB in which the pressure sensor is mounted.

7. The blood pressure meter according to claim 6, wherein at least the region of the first PCB in which the pressure sensor is mounted and the region of the first PCB in which the CPU is mounted are shielded, in the thickness direction, by the display device including a metal plate, wherein the metal plate is disposed extending outward of the first PCB and the second PCB, and wherein the metal plate is disposed on a back surface of the display device, so as to realize hermetic sealing.

8. The blood pressure meter according to claim 1,
wherein the main body includes a bottom wall between the second PCB and the fluid bladder, the bottom wall including a through cylindrical portion extending in the thickness direction so as to constitute a portion of the circumferential wall of the second fluid path, and
wherein the inlet pipe of the pressure sensor and a nipple that is in communication with the fluid bladder are hermetically attached to the cylindrical portion of the bottom wall.

9. The blood pressure meter according to claim 1,
wherein a battery for supplying power to each constituent element of the blood pressure meter is mounted inside the main body, and
wherein the battery continuously occupies a space in which at least the first PCB and the second PCB are disposed in the thickness direction.

10. The blood pressure meter according to claim 9, wherein the first PCB, the pump, the second PCB, and the battery form a rectangular parallelepipedal shaped outer contour as a whole.

11. The blood pressure meter according to claim 2,
wherein the pump is disposed at a position adjacent to the first PCB in the planar direction,
wherein the first fluid path includes an outlet pipe of the pump as a circumferential wall of the first fluid path, and extends straight between the pump and the fluid bladder in parallel to the second fluid path, and
wherein the second PCB extends in a space that is located between the pump and the fluid bladder in the thickness direction and is adjacent to the first fluid path in the planar direction.

12. The blood pressure meter according to claim 11,
wherein a pump driving circuit for driving the pump is mounted on the second PCB,
wherein a region of the second PCB in which the pump driving circuit is mounted is provided to be spaced apart, in the planar direction, from a region of the first PCB in which the pressure sensor is mounted and to oppose the pump, and
wherein a lead wire that electrically connects the pump driving circuit and the pump is connected to an end portion of the pump, the end portion being on an opposite side of the pressure sensor in the planar direction.

13. The blood pressure meter according to claim 1,
wherein the first PCB is disposed between the display device and the second PCB in the thickness direction.

14. The blood pressure meter according to claim 1,
wherein a lower housing is disposed between the second PCB and the fluid bladder in the thickness direction.

15. The blood pressure meter according to claim 1,
wherein the main body comprises an upper housing and a lower housing, and
wherein the lower housing is disposed between the second PCB and the fluid bladder in the thickness direction.

16. The blood pressure meter according to claim 1,
wherein the main body comprises an upper housing and a lower housing, and
wherein the second PCB is disposed within the main body.

17. The blood pressure meter according to claim 1,
wherein the main body comprises an upper housing and a lower housing,
wherein the first PCB is disposed between the upper housing and the second PCB in the thickness direction,
wherein the lower housing is disposed between the second PCB and the fluid bladder in the thickness direction, and
wherein the second PCB is disposed within the main body.

18. The blood pressure meter according to claim 8,
wherein the main body comprises an upper housing and a lower housing, and
wherein the lower housing comprises the bottom wall.

* * * * *